(12) United States Patent
Golz et al.

(10) Patent No.: US 7,465,548 B2
(45) Date of Patent: Dec. 16, 2008

(54) METHODS OF SCREENING FOR POTENTIAL THERAPEUTICS FOR DISEASES ASSOCIATED WITH G-PROTEIN COUPLED RECEPTOR HM74A

(75) Inventors: Stefan Golz, Essen (DE); Ulf Brüggemeier, Leichlingen (DE); Holger Summer, Wuppertal (DE)

(73) Assignee: Bayer Healthcare AG, Leverkusen (DE)

( * ) Notice: Subject to any disclaimer, the term of this patent is extended or adjusted under 35 U.S.C. 154(b) by 0 days.

(21) Appl. No.: 10/544,615

(22) PCT Filed: Feb. 5, 2004

(86) PCT No.: PCT/EP2004/001056

§ 371 (c)(1),
(2), (4) Date: Mar. 22, 2006

(87) PCT Pub. No.: WO2004/071378

PCT Pub. Date: Aug. 26, 2004

(65) Prior Publication Data

US 2006/0160132 A1    Jul. 20, 2006

(30) Foreign Application Priority Data

Feb. 17, 2003    (EP) .................................. 03003534

(51) Int. Cl.
*G01N 33/53* (2006.01)
*G01N 33/567* (2006.01)
*A61K 49/00* (2006.01)

(52) U.S. Cl. ........................... 435/7.1; 435/7.2; 424/9.2

(58) Field of Classification Search ........................ None
See application file for complete search history.

(56) References Cited

U.S. PATENT DOCUMENTS 6,902,902 B2 *    6/2005    Unett et al. .................. 435/7.1

FOREIGN PATENT DOCUMENTS

| WO | WO 98/56820 | 12/1998 |
|---|---|---|
| WO | WO 02/13845 | 2/2002 |
| WO | WO 02/084298 | 10/2002 |

OTHER PUBLICATIONS

Wise, et al., "Molecular Identification of High and Low Affinity Receptors for Nicotinic Acid," Journal of Biological Chemistry, 278 (11): 9869-9874 (2003).
Adams & Cory, "Transgenic models for haemopoietic malignancies," *Biochim. Biophys. Acta 1075*9-31, Apr. 1991.
Dick et al., "Mouse models for human hematopoiesis," *Semin. Immunol. 3*, 367-78, Nov. 1991.
Fricker et al., "Evaluation Tools and Animal Models of Peripheral Neuropathies," *Neurodegenerative Diseases 5*, 72-108, 2008.
Lapidot et al., "Modeling human hematopoiesis in immunodeficient mice," *Lab. Anim. Sci. 43*, 147-50, Apr. 1993.
Martini, "Animal models for inherited peripheral neuropathies," *J. Anat. 191*, 321-36. 1997.
Schuening et al., "Hematopoietic growth factors after allogeneic marrow transplantation in animal studies and clinical trials," *Bone Marrow Transplant. 14 Suppl. 4*, S74-77, 1994.
Srour et al., "Animal models for human hematopoiesis," *J. Hematother. 1*, 143-53, 1992.
Wall & Melzack, eds., Textbook "Animal Models of Neuropathic Pain," pp. 144-148 and pp. 359-369, 1999.

* cited by examiner

*Primary Examiner*—Robert Landsman
(74) *Attorney, Agent, or Firm*—Banner & Witcoff, Ltd.

(57) ABSTRACT

The invention provides a human HM74a which is associated with the disorders of the peripheral and central nervous system, cardiovascular diseases, hematological diseases, cancer, inflammation, urological diseases, respiratory diseases and gastroenterological diseases. The invention also provides assays for the identification of compounds useful in the treatment or prevention of disorders of the peripheral and central nervous system, cardiovascular diseases, hematological diseases, cancer, inflammation, urological diseases, respiratory diseases and gastroenterological diseases. The invention also features compounds which bind to and/or activate or inhibit the activity of HM74a as well as pharmaceutical compositions comprising such compounds.

16 Claims, 2 Drawing Sheets

Fig. 1

SEQ ID NO: 1 atgaatcggcaccatctgcaggatcactttctggaaatagacaagaag
aactgctgtgtgttccgagatgacttcattgtcaaggtgttgccgccg
gtgttggggctggagtttatcttcgggcttctgggcaatggccttgcc
ctgtgatttctgtttccacctcaagtcctggaaatccagccggatt
ttcctgttcaacctggcagtggctgactttctactgatcatctgcctg
cccttcctgatggacaactatgtgaggcgttgggactggaagtttggg
gacatccttgccggctgatgctcttcatgttggctatgaaccgcag
ggcagcatcatcttcctcacggtggtggcggtagacaggtatttccgg
gtggtccatccccaccacgccctgaacaagatctccaatcggacagca
gccatcatctcttgccttctgtggggcatcactattggcctgacagtc
cacctcctgaagaagaagatgccgatccagaatggcggtgcaaatttg
tgcagcagcttcagcatctgccataccttcagtggcacgaagccatg
ttcctcctggagttcttcctgcccctgggcatcatcctgttctgctca
gccagaattatctggagcctgcggcagagacaaatggaccggcatgcc
aagatcaagagagccatcaccttcatcatggtggtggccatcgtcttt
gtcatctgcttccttcccagcgtggttgtgcggatccgcatcttctgg
ctcctgcacacttcgggcacgcagaattgtgaagtgtaccgctcggtg
gacctggcgttctttatcactctcagcttcacctacatgaacagcatg
ctggacccgtggtgtactacttctccagcccatcctttcccaacttc
ttctccactttgatcaaccgctgcctccagaggaagatgacaggtgag
ccagataataaccgcagcacgagcgtcgagctcacaggggaccccaac
aaaaccagaggcgctccagaggcgttaatggccaactccggtgagcca
tggagcccctcttatctgggcccaacctctccttaa

Fig. 2
SEQ ID NO: 2

MNRHHLQDHFLEIDKKNCCVFRDDFIVKVLPPVLGLEFIFGLLGNGLA
LWIFCFHLKSWKSSRIFLFNLAVADFLLIICLPFLMDNYVRRWDWKFG
DIPCRLMLFMLAMNRQGSIIFLTVVAVDRYFRVVHPHHALNKISNRTA
AIISCLLWGITIGLTVHLLKKKMPIQNGGANLCSSFSICHTFQWHEAM
FLLEFFLPLGIILFCSARIIWSLRQRQMDRHAKIKRAITFIMVVAIVF
VICFLPSVVVRIRIFWLLHTSGTQNCEVYRSVDLAFFITLSFTYMNSM
LDPVVYYFSSPSFPNFFSTLINRCLQRKMTGEPDNNRSTSVELTGDPN
KTRGAPEALMANSGEPWSPSYLGPTSP

Fig. 3
SEQ ID NO: 3

5'-cagcttcagcatctgccata-3'

Fig. 4
SEQ ID NO: 4

5'-caggaagaactccaggagga-3'

Fig. 5
SEQ ID NO: 5

5'-cttccagtggcacgaagccatgt-3'

SEQUENCE LISTING

```
<160> NUMBER OF SEQ ID NOS: 5

<210> SEQ ID NO 1
<211> LENGTH: 1092
<212> TYPE: DNA
<213> ORGANISM: Homo sapiens

<400> SEQUENCE: 1
atgaatcggc accatctgca ggatcacttt ctggaaatag acaagaagaa ctgctgtgtg      60
ttccgagatg acttcattgt caaggtgttg ccgccggtgt tggggctgga gtttatcttc     120
gggcttctgg gcaatggcct tgccctgtgg attttctgtt tccacctcaa gtcctggaaa     180
tccagccgga ttttcctgtt caacctggca gtggctgact ttctactgat catctgcctg     240
cccttcctga tggacaacta tgtgaggcgt tgggactgga gtttggggga catcccttgc     300
cggctgatgc tcttcatgtt ggctatgaac cgccagggca gcatcatctt cctcacggtg     360
gtggcggtag acaggtattt ccgggtggtc catcccacc acgccctgaa caagatctcc     420
aatcggacag cagccatcat ctcttgcctt ctgtgggca tcactattgg cctgacagtc     480
cacctcctga agaagaagat gccgatccag aatggcggtg caaatttgtg cagcagcttc     540
agcatctgcc ataccttcca gtggcacgaa gccatgttcc tcctggagtt cttcctgccc     600
ctgggcatca tcctgttctg ctcagccaga attatctgga gcctgcggca gagacaaatg     660
gaccggcatg ccaagatcaa gagagccatc acccttcatca tggtggtggc catcgtcttt     720
gtcatctgct tccttcccag cgtggttgtg cggatccgca tcttctggct cctgcacact     780
tcgggcacgc agaattgtga agtgtaccgc tcggtggacc tggcgttctt tatcactctc     840
agcttcacct acatgaacag catgctggac cccgtggtgt actacttctc cagcccatcc     900
tttcccaact tcttctccac tttgatcaac cgctgcctcc agaggaagat gacaggtgag     960
```

```
ccagataata accgcagcac gagcgtcgag ctcacagggg accccaacaa aaccagaggc    1020
gctccagagg cgttaatggc caactccggt gagccatgga gcccctctta tctgggccca    1080
acctctcctt aa                                                        1092
```

<210> SEQ ID NO 2
<211> LENGTH: 363
<212> TYPE: PRT
<213> ORGANISM: Homo sapiens

<400> SEQUENCE: 2

| | | | | | | | | | | | | | | |
|---|---|---|---|---|---|---|---|---|---|---|---|---|---|---|
| Met | Asn | Arg | His | His | Leu | Gln | Asp | His | Phe | Leu | Glu | Ile | Asp | Lys | Lys |
| 1 | | | | 5 | | | | | 10 | | | | | 15 | |
| Asn | Cys | Cys | Val | Phe | Arg | Asp | Asp | Phe | Ile | Val | Lys | Val | Leu | Pro | Pro |
| | | | 20 | | | | | 25 | | | | | 30 | | |
| Val | Leu | Gly | Leu | Glu | Phe | Ile | Phe | Gly | Leu | Leu | Gly | Asn | Gly | Leu | Ala |
| | | | 35 | | | | | 40 | | | | | 45 | | |
| Leu | Trp | Ile | Phe | Cys | Phe | His | Leu | Lys | Ser | Trp | Lys | Ser | Ser | Arg | Ile |
| 50 | | | | | 55 | | | | | 60 | | | | | |
| Phe | Leu | Phe | Asn | Leu | Ala | Val | Ala | Asp | Phe | Leu | Leu | Ile | Ile | Cys | Leu |
| 65 | | | | | 70 | | | | | 75 | | | | | 80 |
| Pro | Phe | Leu | Met | Asp | Asn | Tyr | Val | Arg | Arg | Trp | Asp | Trp | Lys | Phe | Gly |
| | | | | 85 | | | | | 90 | | | | | 95 | |
| Asp | Ile | Pro | Cys | Arg | Leu | Met | Leu | Phe | Met | Leu | Ala | Met | Asn | Arg | Gln |
| | | | 100 | | | | | 105 | | | | | 110 | | |
| Gly | Ser | Ile | Ile | Phe | Leu | Thr | Val | Val | Ala | Val | Asp | Arg | Tyr | Phe | Arg |
| | | | 115 | | | | | 120 | | | | | 125 | | |
| Val | Val | His | Pro | His | His | Ala | Leu | Asn | Lys | Ile | Ser | Asn | Arg | Thr | Ala |
| | 130 | | | | | 135 | | | | | 140 | | | | |
| Ala | Ile | Ile | Ser | Cys | Leu | Leu | Trp | Gly | Ile | Thr | Ile | Gly | Leu | Thr | Val |
| 145 | | | | | 150 | | | | | 155 | | | | | 160 |
| His | Leu | Leu | Lys | Lys | Lys | Met | Pro | Ile | Gln | Asn | Gly | Gly | Ala | Asn | Leu |
| | | | | 165 | | | | | 170 | | | | | 175 | |
| Cys | Ser | Ser | Phe | Ser | Ile | Cys | His | Thr | Phe | Gln | Trp | His | Glu | Ala | Met |
| | | | 180 | | | | | 185 | | | | | 190 | | |
| Phe | Leu | Leu | Glu | Phe | Phe | Leu | Pro | Leu | Gly | Ile | Ile | Leu | Phe | Cys | Ser |
| | | | 195 | | | | | 200 | | | | | 205 | | |
| Ala | Arg | Ile | Ile | Trp | Ser | Leu | Arg | Gln | Arg | Gln | Met | Asp | Arg | His | Ala |
| | 210 | | | | | 215 | | | | | 220 | | | | |
| Lys | Ile | Lys | Arg | Ala | Ile | Thr | Phe | Ile | Met | Val | Val | Ala | Ile | Val | Phe |
| 225 | | | | | 230 | | | | | 235 | | | | | 240 |
| Val | Ile | Cys | Phe | Leu | Pro | Ser | Val | Val | Val | Arg | Ile | Arg | Ile | Phe | Trp |
| | | | | 245 | | | | | 250 | | | | | 255 | |
| Leu | Leu | His | Thr | Ser | Gly | Thr | Gln | Asn | Cys | Glu | Val | Tyr | Arg | Ser | Val |
| | | | 260 | | | | | 265 | | | | | 270 | | |
| Asp | Leu | Ala | Phe | Phe | Ile | Thr | Leu | Ser | Phe | Thr | Tyr | Met | Asn | Ser | Met |
| | | | 275 | | | | | 280 | | | | | 285 | | |
| Leu | Asp | Pro | Val | Val | Tyr | Tyr | Phe | Ser | Ser | Pro | Ser | Phe | Pro | Asn | Phe |
| | 290 | | | | | 295 | | | | | 300 | | | | |
| Phe | Ser | Thr | Leu | Ile | Asn | Arg | Cys | Leu | Gln | Arg | Lys | Met | Thr | Gly | Glu |
| 305 | | | | | 310 | | | | | 315 | | | | | 320 |
| Pro | Asp | Asn | Asn | Arg | Ser | Thr | Ser | Val | Glu | Leu | Thr | Gly | Asp | Pro | Asn |
| | | | | 325 | | | | | 330 | | | | | 335 | |
| Lys | Thr | Arg | Gly | Ala | Pro | Glu | Ala | Leu | Met | Ala | Asn | Ser | Gly | Glu | Pro |
| | | | 340 | | | | | 345 | | | | | 350 | | |

```
Trp Ser Pro Ser Tyr Leu Gly Pro Thr Ser Pro
        355                 360

<210> SEQ ID NO 3
<211> LENGTH: 20
<212> TYPE: DNA
<213> ORGANISM: Artificial
<220> FEATURE:
<223> OTHER INFORMATION: Forward primer: Primer1

<400> SEQUENCE: 3
cagcttcagc atctgccata                                                     20

<210> SEQ ID NO 4
<211> LENGTH: 20
<212> TYPE: DNA
<213> ORGANISM: Artificial
<220> FEATURE:
<223> OTHER INFORMATION: Reverse primer: Primer2

<400> SEQUENCE: 4
caggaagaac tccaggagga                                                     20

<210> SEQ ID NO 5
<211> LENGTH: 23
<212> TYPE: DNA
<213> ORGANISM: Artificial
<220> FEATURE:
<223> OTHER INFORMATION: Probe1

<400> SEQUENCE: 5
cttccagtgg cacgaagcca tgt                                                 23
```

METHODS OF SCREENING FOR POTENTIAL THERAPEUTICS FOR DISEASES ASSOCIATED WITH G-PROTEIN COUPLED RECEPTOR HM74A

This application is a 371 of PCT/EP2004/001056, filed Feb. 5, 2004.

TECHNICAL FIELD OF THE INVENTION

The present invention is in the field of molecular biology, more particularly, the present invention relates to nucleic acid sequences and amino acid sequences of a human HM74a and its regulation for the treatment of disorders of the peripheral and central nervous system, cardiovascular diseases, hematological diseases, cancer, inflammation, urological diseases, respiratory diseases and gastroenterological diseases in mammals.

BACKGROUND OF THE INVENTION

G-Protein Coupled Receptors

HM74a is a seven transmembrane G protein coupled receptor (GPCR) [Pike et al., (2003), Peffer et al., (2001), WO200022129, WO0136471, WO0213845]. Many medically significant biological processes are mediated by signal transduction path-ways that involve G-proteins [Lefkowitz, (1991)]. The family of G-protein coupled receptors (GPCRs) includes receptors for hormones, neurotransmitters, growth factors, and viruses. Specific examples of GPCRs include receptors for such diverse agents as dopamine, calcitonine, adrenergic hormones, endotheline, cAMP, adenosine, acetylcholine, serotonine, histamine, thrombin, kinine, follicle stimulating hormone, opsins, endothelial differentiation gene-1, rhodopsins, odorants, cytomegalovirus, G-proteins themselves, effector proteins such as phospholipase C, adenyl cyclase, and phosphodiesterase, and actuator proteins such as protein kinase A and protein kinase C.

GPCRs possess seven conserved membrane-spanning domains connecting at least eight divergent hydrophilic loops. GPCRs, also known as seven transmembrane, 7TM, receptors, have been characterized as including these seven conserved hydrophobic stretches of about 20 to 30 amino acids, connecting at least eight divergent hydrophilic loops. Most GPCRs have single conserved cysteine residues in each of the first two extracellular loops, which form disulfide bonds that are believed to stabilize functional protein structure. The seven transmembrane regions are designated as TM1, TM2, TM3, TM4, TM5, TM6, and TM7. TM3 is being implicated with signal transduction. Phosphorylation and lipidation (palmitylation or farnesylation) of cysteine residues can influence signal transduction of some GPCRs. Most GPCRs contain potential phosphorylation sites within the third cytoplasmic loop and/or the carboxy terminus. For several GPCRs, such as the beta-adrenergic receptor, phosphorylation by protein kinase A and/or specific receptor kinases mediates receptor desensitization.

For some receptors, the ligand binding sites of GPCRs are believed to comprise hydrophilic sockets formed by several GPCR transmembrane domains. The hydrophilic sockets are surrounded by hydrophobic residues of the GPCRs. The hydrophilic side of each GPCR transmembrane helix is postulated to face inward and form a polar ligand binding site. TM3 is being implicated with several GPCRs as having a ligand binding site, such as the TM3 aspartate residue. TMS serines, a TM6 asparagine, and TM6 or TM7 phenylalanines or tyrosines also are implicated in ligand binding.

GPCRs are coupled inside the cell by heterotrimeric G-proteins to various intracellular enzymes, ion channels, and transporters. Different G-protein alpha-subunits preferentially stimulate particular effectors to modulate various biological functions in a cell. Phosphorylation of cytoplasmic residues of GPCRs is an important mechanism for the regulation of some GPCRs. For example, in one form of signal transduction, the effect of hormone binding is the activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein exchanges GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

Over the past 15 years, nearly 350 therapeutic agents targeting 7TM receptors have been successfully introduced into the market. This indicates that these receptors have an established, proven history as therapeutic targets. Clearly, there is a need for identification and characterization of further receptors which can play a role in preventing, ameliorating, or correcting dysfunctions or diseases including, but not limited to, infections such as bacterial, fungal, protozoan, and viral infections, particularly those caused by HIV viruses, cancers, allergies including asthma, cardiovascular diseases including acute heart failure, hypotension, hypertension, angina pectoris, myocardial infarction, hematological diseases, genitourinary diseases including urinary incontinence and benign prostate hyperplasia, osteoporosis, and peripheral and central nervous system disorders including pain, Alzheimer's disease and Parkinson's disease.

TaqMan-Technology/Expression Profiling

TaqMan is a recently developed technique, in which the release of a fluorescent reporter dye from a hybridisation probe in real-time during a polymerase chain reaction (PCR) is proportional to the accumulation of the PCR product. Quantification is based on the early, linear part of the reaction, and by determining the threshold cycle (CT), at which fluorescence above background is first detected.

Gene expression technologies may be useful in several areas of drug discovery and development, such as target identification, lead optimization, and identification of mechanisms of action. The TaqMan technology can be used to compare differences between expression profiles of normal tissue and diseased tissue. Expression pro-filing has been used in identifying genes, which are up- or downregulated in a variety of diseases. An interesting application of expression profiling is temporal monitoring of changes in gene expression during disease progression and drug treatment or in patients versus healthy individuals. The premise in this approach is that changes in pattern of gene expression in response to physiological or environmental stimuli (e.g., drugs) may serve as indirect clues about disease-causing genes or drug targets. Moreover, the effects of drugs with established efficacy on global gene expression patterns may provide a guidepost, or a genetic signature, against which a new drug candidate can be compared.

HM74a

The nucleotide sequence of HM74a is accessible in public databases by the accession number AB083632 and is given in SEQ ID NO:1. The amino acid sequence of HM74a is depicted-in SEQ ID NO:2.

The HM74a receptor was identified by Matsushima et al. (1993) as a G-Protein coupled receptor. The predicted amino acid sequence of HM74a protein contains the 7 transmembrane domains characteristic of G protein-coupled receptors. HM74a is a receptor for nicotinic acid (niacin) [(Pfeffer et al., (2001); Pike et al., (2003)]. The receptor HM74a is also described in patents WO200022129, WO0136471 and WO0213845. The human HM74a receptor shows the highest homology to the mus musculus receptor HM74 (83%) as shown above.

SUMMARY OF THE INVENTION

The invention relates to novel disease associations of HM74a polypeptides and polynucleotides. The invention also relates to novel methods of screening for therapeutic agents for the treatment of disorders of the peripheral and central nervous system, cardiovascular diseases, hematological diseases, cancer, inflammation, urological diseases, respiratory diseases and gastroenterological diseases in a mammal. The invention also relates to pharmaceutical compositions for the treatment of disorders of the peripheral and central nervous system, cardiovascular diseases, hematological diseases, cancer, inflammation, urological diseases, respiratory diseases and gastroenterological diseases in a mammal comprising a HM74a polypeptide, a HM74a polynucleotide, or regulators of HM74a or modulators of HM74a activity. The invention further comprises methods of diagnosing disorders of the peripheral and central nervous system, cardiovascular diseases, hematological diseases, cancer, inflammation, urological diseases, respiratory diseases and gastroenterological diseases in a mammal.

BRIEF DESCRIPTION OF THE DRAWINGS

FIG. 1 shows the nucleotide sequence of a HM74a receptor polynucleotide (SEQ ID NO:1).

FIG. 2 shows the amino acid sequence of a HM74a receptor polypeptide (SEQ ID NO:2).

FIG. 3 shows the nucleotide sequence of a primer useful for the invention (SEQ ID NO:3).

FIG. 4 shows the nucleotide sequence of a primer useful for the invention (SEQ ID NO:4).

FIG. 5 shows a nucleotide sequence useful as a probe to detect proteins of the invention (SEQ ID NO:5).

DETAILED DESCRIPTION OF THE INVENTION

Definition of Terms

An "oligonucleotide" is a stretch of nucleotide residues which has a sufficient number of bases to be used as an oligomer, amplimer or probe in a polymerase chain reaction (PCR). Oligonucleotides are prepared from genomic or cDNA sequence and are used to amplify, reveal, or confirm the presence of a similar DNA or RNA in a particular cell or tissue. Oligonucleotides or oligomers comprise portions of a DNA sequence having at least about 10 nucleotides and as many as about 35 nucleotides, preferably about 25 nucleotides.

"Probes" may be derived from naturally occurring or recombinant single- or double-stranded nucleic acids or may be chemically synthesized. They are useful in detecting the presence of identical or similar sequences. Such probes may be labeled with reporter molecules using nick translation, Klenow fill-in reaction, PCR or other methods well known in the art. Nucleic acid probes may be used in southern, northern or in situ hybridizations to determine whether DNA or RNA encoding a certain protein is present in a cell type, tissue, or organ.

A "fragment of a polynucleotide" is a nucleic acid that comprises all or any part of a given nucleotide molecule, the fragment having fewer nucleotides than about 6 kb, preferably fewer than about 1 kb.

"Reporter molecules" are radionuclides, enzymes, fluorescent, chemiluminescent, or chromogenic agents which associate with a particular nucleotide or amino acid sequence, thereby establishing the presence of a certain sequence, or allowing for the quantification of a certain sequence.

"Chimeric" molecules may be constructed by introducing all or part of the nucleotide sequence of this invention into a vector containing additional nucleic acid sequence which might be expected to change any one or several of the following HM74a characteristics: cellular location, distribution, ligand-binding affinities, interchain affinities, degradation/turnover rate, signaling, etc.

"Active", with respect to a HM74a polypeptide, refers to those forms, fragments, or domains of a HM74a polypeptide which retain the biological and/or antigenic activity of a HM74a polypeptide.

"Naturally occurring HM74a polypeptide" refers to a polypeptide produced by cells which have not been genetically engineered and specifically contemplates various polypeptides arising from post-translational modifications of the polypeptide including but not limited to acetylation, carboxylation, glycosylation, phosphorylation, lipidation and acylation.

"Derivative" refers to polypeptides which have been chemically modified by techniques such as ubiquitination, labeling (see above), pegylation (derivatization with polyethylene glycol), and chemical insertion or substitution of amino acids such as ornithine which do not normally occur in human proteins.

"Conservative amino acid substitutions" result from replacing one amino acid with another having similar structural and/or chemical properties, such as the replacement of a leucine with an isoleucine or valine, an aspartate with a glutamate, or a threonine with a serine.

"Insertions" or "deletions" are typically in the range of about 1 to 5 amino acids. The variation allowed may be experimentally determined by producing the peptide synthetically while systematically making insertions, deletions, or substitutions of nucleotides in the sequence using recombinant DNA techniques.

A "signal sequence" or "leader sequence" can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. Oligopeptides comprise a stretch of amino acid residues of at least 3, 5, 10 amino acids and at most 10, 15, 25 amino acids, typically of at least 9 to 13 amino acids, and of sufficient length to display biological and/or antigenic activity.

"Inhibitor" is any substance which retards or prevents a chemical or physiological reaction or response. Common inhibitors include but are not limited to antisense molecules, antibodies, and antagonists.

"Standard expression" is a quantitative or qualitative measurement for comparison. It is based on a statistically appropriate number of normal samples and is created to use as a basis of comparison when performing diagnostic assays, running clinical trials, or following patient treatment profiles.

"Animal" as used herein may be defined to include human, domestic (e.g., cats, dogs, etc.), agricultural (e.g., cows, horses, sheep, etc.) or test species (e.g., mouse, rat, rabbit, etc.).

A "HM74a polynucleotide", within the meaning of the invention, shall be understood as being a nucleic acid molecule selected from a group consisting of
(i) nucleic acid molecules encoding a polypeptide comprising the amino acid sequence of SEQ ID NO: 2,
(ii) nucleic acid molecules comprising the sequence of SEQ ID NO: 1,
(iii) nucleic acid molecules having the sequence of SEQ ID NO: 1,
(iv) nucleic acid molecules the complementary strand of which hybridizes under stringent conditions to a nucleic acid molecule of (i), (ii), or (iii); and
(v) nucleic acid molecules the sequence of which differs from the sequence of a nucleic acid molecule of (iii) due to the degeneracy of the genetic code;

wherein the polypeptide encoded by said nucleic acid molecule has HM74a activity A "4HM74a polypeptide", within the meaning of the invention, shall be understood as being a polypeptide selected from a group consisting of
(i) polypeptides having the sequence of SEQ ID NO: 2,
(ii) polypeptides comprising the sequence of SEQ ID NO: 2,
(iii) polypeptides encoded by HM74a polynucleotides; and
(iv) polypeptides which show at least 99%, 98%, 95%, 90%, or 80% homology with a polypeptide of (i), (ii), or (iii);

wherein said polypeptide has HM74a activity:

The nucleotide sequences encoding a HM74a (or their complement) have numerous applications in techniques known to those skilled in the art of molecular biology. These techniques include use as hybridization probes, use in the construction of oligomers for PCR, use for chromosome and gene mapping, use in the recombinant production of HM74a, and use in generation of antisense DNA or RNA, their chemical analogs and the like. Uses of nucleotides encoding a HM74a disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of HM74a—encoding nucleotide sequences may be produced. Some of these will only bear minimal homology to the nucleotide sequence of the known and naturally occurring HM74a. The invention has specifically contemplated each and every possible variation of nucleotide sequence that could be made by selecting combinations based on possible codon choices. These combinations are made in accordance with the standard triplet genetic code as applied to the nucleotide sequence of naturally occurring HM74a, and all such variations are to be considered as being specifically disclosed.

Although the nucleotide sequences which encode a HM74a, its derivatives or its variants are preferably capable of hybridizing to the nucleotide sequence of the naturally occurring HM74a polynucleotide under stringent conditions, it may be advantageous to produce nucleotide sequences encoding HM74a polypeptides or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding a HM74a polypeptide and/or its derivatives without altering the encoded amino acid sequence include the production of RNA transcripts having more desirable properties, such as a greater half-life, than transcripts produced from the naturally occurring sequence.

Nucleotide sequences encoding a HM74a polypeptide may be joined to a variety of other nucleotide sequences by means of well established recombinant DNA techniques. Useful nucleotide sequences for joining to HM74a polynucleotides include an assortment of cloning vectors such as plasmids, cosmids, lambda phage derivatives, phagemids, and the like. Vectors of interest include expression vectors, replication vectors, probe generation vectors, sequencing vectors, etc. In general, vectors of interest may contain an origin of replication functional in at least one organism, convenient restriction endonuclease sensitive sites, and selectable markers for one or more host cell systems.

Another aspect of the subject invention is to provide for HM74a-specific hybridization probes capable of hybridizing with naturally occurring nucleotide sequences encoding HM74a. Such probes may also be used for the detection of similar GPCR encoding sequences and should preferably show at least 40% nucleotide identity to HM74a polynucleotides. The hybridization probes of the subject invention may be derived from the nucleotide sequence presented as SEQ ID NO: 1 or from genomic sequences including promoter, enhancers or introns of the native gene. Hybridization probes may be labelled by a variety of reporter molecules using techniques well known in the art.

It will be recognized that many deletional or mutational analogs of HM74a polynucleotides will be effective hybridization probes for HM74a polynucleotides. Accordingly, the invention relates to nucleic acid sequences that hybridize with such HM74a encoding nucleic acid sequences under stringent conditions.

"Stringent conditions" refers to conditions that allow for the hybridization of substantially related nucleic acid sequences. For instance, such conditions will generally allow hybridization of sequence with at least about 85% sequence identity, preferably with at least about 90% sequence identity, more preferably with at least about 95% sequence identity. Hybridization conditions and probes can be adjusted in well-characterized ways to achieve selective hybridization of human-derived probes. Stringent conditions, within the meaning of the invention are 65° C. in a buffer containing 1 mM EDTA, 0.5 M NaHPO$_4$ (pH 7.2), 7% (w/v) SDS.

Nucleic acid molecules that will hybridize to HM74a polynucleotides under stringent conditions can be identified functionally. Without limitation, examples of the uses for hybridization probes include: histochemical uses such as identifying tissues that express HM74a; measuring mRNA levels, for instance to identity a sample's tissue type or to identify cells that express abnormal levels of HM74a; and detecting polymorphisms of HM74a.

PCR provides additional uses for oligonucleotides based upon the nucleotide sequence which encodes HM74a. Such probes used in PCR may be of recombinant origin, chemically synthesized, or a mixture of both. Oligomers may comprise discrete nucleotide sequences employed under optimized conditions for identification of HM74a in specific tissues or diagnostic use. The same two oligomers, a nested set of oligomers, or even a degenerate pool of oligomers may be employed under less stringent conditions for identification of closely related DNAs or RNAs.

Rules for designing polymerase chain reaction (PCR) primers are now established, as reviewed by PCR Protocols. Degenerate primers, i.e., preparations of primers that are heterogeneous at given sequence locations, can be designed to amplify nucleic acid sequences that are highly homologous to, but not identical with HM74a. Strategies are now available that allow for only one of the primers to be required to specifically hybridize with a known sequence. For example, appropriate nucleic acid primers can be ligated to the nucleic acid sought to be amplified to provide the hybridization partner for one of the primers. In this way, only one of the primers need be based on the sequence of the nucleic acid sought to be amplified.

PCR methods for amplifying nucleic acid will utilize at least two primers. One of these primers will be capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known.

Other means of producing specific hybridization probes for HM74a include the cloning of nucleic acid sequences encoding HM74a or HM74a derivatives into vectors for the production of mRNA probes. Such vectors are known in the art, are commercially available and may be used to synthesize RNA probes in vitro by means of the addition of the appropriate RNA polymerase as T7 or SP6 RNA polymerase and the appropriate reporter molecules.

It is possible to produce a DNA sequence, or portions thereof, entirely by synthetic chemistry. After synthesis, the nucleic acid sequence can be inserted into any of the many available DNA vectors and their respective host cells using techniques which are well known in the art. Moreover, synthetic chemistry may be used to introduce mutations into the nucleotide sequence. Alternately, a portion of sequence in which a mutation is desired can be synthesized and recombined with longer portion of an existing genomic or recombinant sequence.

HM74a polynucleotides may be used to produce a purified oligo-or polypeptide using well known methods of recombinant DNA technology. The oligopeptide may be expressed in a variety of host cells, either prokaryotic or eukaryotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Quantitative Determinations of Nucleic Acids

An important step in the molecular genetic analysis of human disease is often the enumeration of the copy number of a nucleis acid or the relative expression of a gene in particular tissues.

Several different approaches are currently available to make quantitative determinations of nucleic acids. Chromosome-based techniques, such as comparative genomic hybridization (CGH) and fluorescent in situ hybridization (FISH) facilitate efforts to cytogenetically localize genomic regions that are altered in tumor cells. Regions of genomic alteration can be narrowed further using loss of heterozygosity analysis (LOH), in which disease DNA is analyzed and compared with normal DNA for the loss of a heterozygous polymorphic marker. The first experiments used restriction fragment length polymorphisms (RFLPs) [Johnson, (1989)], or hyper-variable minisatellite DNA [Barnes, 2000]. In recent years LOH has been performed primarily using PCR amplification of microsatellite markers and electrophoresis of the radio labelled [Jeffreys, (1985)] or fluorescently labelled PCR products [Weber, (1990)] and compared between paired normal and disease DNAs.

A number of other methods have also been developed to quantify nucleic acids [Gergen, (1992)]. More recently, PCR and RT-PCR methods have been developed which are capable of measuring the amount of a nucleic acid in a sample. One approach, for example, measures PCR product quantity in the log phase of the reaction before the formation of reaction products plateaus [Thomas, (1980)].

A gene sequence contained in all samples at relatively constant quantity is typically utilized for sample amplification efficiency normalization. This approach, however, suffers from several drawbacks. The method requires that each sample has equal input amounts of the nucleic acid and that the amplification efficiency between samples is identical until the time of analysis. Furthermore, it is difficult using the conventional methods of PCR quantitation such as gel electrophoresis or plate capture hybridization to determine that all samples are in fact analyzed during the log phase of the reaction as required by the method.

Another method called quantitative competitive (QC)-PCR, as the name implies, relies on the inclusion of an internal control competitor in each reaction [Piatak, (1993), BioTechniques]. The efficiency of each reaction is normalized to the internal competitor. A known amount of internal competitor is typically added to each sample. The unknown target PCR product is compared with the known competitor PCR product to obtain relative quantitation. A difficulty with this general approach lies in developing an internal control that amplifies with the same efficiency than the target molecule.

5' Fluorogenic Nuclease Assays

Fluorogenic nuclease assays are a real time quantitation method that uses a probe to monitor formation of amplification product. The basis for this method of monitoring the formation of amplification product is to measure continuously PCR product accumulation using a dual-labelled fluorogenic oligonucleotide probe, an approach frequently referred to in the literature simply as the "TaqMan method" [Piatak, (1993), Science; Heid, (1996); Gibson, (1996); Holland. (1991)].

The probe used in such assays is typically a short (about 20-25 bases) oligonucleotide that is labeled with two different fluorescent dyes. The 5' terminus of the probe is attached to a reporter dye and the 3' terminus is attached to a quenching dye, although the dyes could be attached at other locations on the probe as well. The probe is designed to have at least substantial sequence complementarity with the probe binding site. Upstream and downstream PCR primers which bind to flanking regions of the locus are added to the reaction mixture. When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter from the oligonucleotide-quencher and resulting in an increase of reporter emission intensity which can be measured by an appropriate detector.

One detector which is specifically adapted for measuring fluorescence emissions such as those created during a fluorogenic assay is the ABI 7700 or 4700 HT manufactured by Applied Biosystems, Inc. in Foster City, Calif. The ABI 7700 uses fiber optics connected with each well in a 96- or 384 well PCR tube arrangement. The instrument includes a laser for exciting the labels and is capable of measuring the fluorescence spectra intensity from each tube with continuous monitoring during PCR amplification. Each tube is re-examined every 8.5 seconds.

Computer software provided with the instrument is capable of recording the fluorescence intensity of reporter and quencher over the course of the amplification. The recorded values will then be used to calculate the increase in normalized reporter emission intensity on a continuous basis. The increase in emission intensity is plotted versus time, i.e., the number of amplification cycles, to produce a continuous measure of amplification. To quantify the locus in each amplification reaction, the amplification plot is examined at a point during the log phase of product accumulation. This is accomplished by assigning a fluorescence threshold intensity above background and determining the point at which each amplification plot crosses the threshold (defined as the threshold cycle number or Ct). Differences in threshold cycle number are used to quantify the relative amount of PCR target contained within each tube. Assuming that each reaction functions at 100% PCR efficiency, a difference of one Ct represents a two-fold difference in the amount of starting template. The fluorescence value can be used in conjunction with a standard curve to determine the amount of amplification product present.

Non-Probe-Based Detection Methods

A variety of options are available for measuring the amplification products as they are formed. One method utilizes labels, such as dyes, which only bind to double stranded DNA. In this type of approach, amplification product (which is double stranded) binds dye molecules in solution to form a complex. With the appropriate dyes, it is possible to distinguish between dye molecules free in solution and dye molecules bound to amplification product. For example, certain dyes fluoresce only when bound to amplification product. Examples of dyes which can be used in methods of this general type include, but are not limited to, Syber Green.™ and Pico Green from Molecular Probes, Inc. of Eugene, Oreg., ethidium bromide, propidium iodide, chromomycin, acridine orange, Hoechst 33258, Toto-1, Yoyo-1, DAPI (4',6-diamidino-2-phenylindole hydrochloride).

Another real time detection technique measures alteration in energy fluorescence energy transfer between fluorophors conjugated with PCR primers [Livak, (1995)].

Probe-Based Detection Methods

These detection methods involve some alteration to the structure or conformation of a probe hybridized to the locus between the amplification primer pair. In some instances, the alteration is caused by the template-dependent extension catalyzed by a nucleic acid polymerase during the amplification process. The alteration generates a detectable signal which is an indirect measure of the amount of amplification product formed.

For example, some methods involve the degradation or digestion of the probe during the extension reaction. These methods are a consequence of the 5'-3' nuclease activity associated with some nucleic acid polymerases. Polymerases having this activity cleave mononucleotides or small oligonucleotides from an oligonucleotide probe annealed to its complementary sequence located within the locus.

The 3' end of the upstream primer provides the initial binding site for the nucleic acid polymerase. As the polymerase catalyzes extension of the upstream primer and encounters the bound probe, the nucleic acid polymerase displaces a portion of the 5' end of the probe and through its nuclease activity cleaves mononucleotides or oligonucleotides from the probe.

The upstream primer and the probe can be designed such that they anneal to the complementary strand in close proximity to one another. In fact, the 3' end of the upstream primer and the 5' end of the probe may abut one another. In this situation, extension of the upstream primer is not necessary in order for the nucleic acid polymerase to begin cleaving the probe. In the case in which intervening nucleotides separate the upstream primer and the probe, extension of the primer is necessary before the nucleic acid polymerase encounters the 5' end of the probe. Once contact occurs and polymerization continues, the 5'-3' exonuclease activity of the nucleic acid polymerase begins cleaving mononucleotides or oligonucleotides from the 5' end of the probe. Digestion of the probe continues until the remaining portion of the probe dissociates from the complementary strand.

In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product.

Probes

The labeled probe is selected so that its sequence is substantially complementary to a segment of the test locus or a reference locus. As indicated above, the nucleic acid site to which the probe binds should be located between the primer binding sites for the upstream and downstream amplification primers.

Primers

The primers used in the amplification are selected so as to be capable of hybridizing to sequences at flanking regions of the locus being amplified. The primers are chosen to have at least substantial complementarity with the different strands of the nucleic acid being amplified. When a probe is utilized to detect the formation of amplification products, the primers are selected in such that they flank the probe, i.e. are located upstream and downstream of the probe.

The primer must have sufficient length so that it is capable of priming the synthesis of extension products in the presence of an agent for polymerization. The length and composition of the primer depends on many parameters, including, for example, the temperature at which the annealing reaction is conducted, proximity of the probe binding site to that of the primer, relative concentrations of the primer and probe and the particular nucleic acid composition of the probe. Typically the primer includes 15-30 nucleotides. However, the length of the primer may be more or less depending on the complexity of the primer binding site and the factors listed above.

Labels for Probes and Primers

The labels used for labeling the probes or primers of the current invention and which can provide the signal corresponding to the quantity of amplification product can take a variety of forms. As indicated above with regard to the 5' fluorogenic nuclease method, a fluorescent signal is one signal which can be measured. However, measurements may also be made, for example, by monitoring radioactivity, colorimetry, absorption, magnetic parameters, or enzymatic activity. Thus, labels which can be employed include, but are not limited to, fluorophors, chromophores, radioactive isotopes, electron dense reagents, enzymes, and ligands having specific binding partners (e.g., biotin-avidin).

Monitoring changes in fluorescence is a particularly useful way to monitor the accumulation of amplification products. A number of labels useful for attachment to probes or primers are commercially available including fluorescein and various fluorescein derivatives such as FAM, HEX, TET and JOE (all which are available from Applied Biosystems, Foster City, Calif.); lucifer yellow, and coumarin derivatives.

Labels may be attached to the probe or primer using a variety of techniques and can be attached at the 5' end, and/or the 3' end and/or at an internal nucleotide. The label can also be attached to spacer arms of various sizes which are attached to the probe or primer. These spacer arms are useful for obtaining a desired distance between multiple labels attached to the probe or primer.

In some instances, a single label may be utilized; whereas, in other instances, such as with the 5' fluorogenic nuclease assays for example, two or more labels are attached to the probe. In cases wherein the probe includes multiple labels, it is generally advisable to maintain spacing between the labels which is sufficient to permit separation of the labels during digestion of the probe through the 5'-3' nuclease activity of the nucleic acid polymerase.

Patients Exhibiting Symptoms of Disease

A number of diseases are associated with changes in the copy number of a certain gene. For patients having symptoms of a disease, the real-time PCR method can be used to determine if the patient has copy number alterations which are known to be linked with diseases that are associated with the symptoms the patient has.

HM74a Expression

HM74a Fusion Proteins

Fusion proteins are useful for generating antibodies against HM74a polypeptides and for use in various assay systems. For example, fusion proteins can be used to identify proteins which interact with portions of HM74a polypeptides. Protein affinity chromatography or library-based assays for protein-protein interactions, such as the yeast two-hybrid or phage display systems, can be used for this purpose. Such methods are well known in the art and also can be used as drug screens.

A HM74a fusion protein comprises two polypeptide segments fused together by means of a peptide bond. The first polypeptide segment can comprise at least 54, 75, 100, 125, 139, 150, 175, 200, 225, 250, or 275 contiguous amino acids of SEQ ID NO: 2 or of a biologically active variant, such as those described above. The first polypeptide segment also can comprise full-length HM74a.

The second polypeptide segment can be a full-length protein or a protein fragment. Proteins commonly used in fusion protein construction include, but are not limited to β galactosidase, β-glucuronidase, green fluorescent protein (GFP), autofluorescent proteins, including blue fluorescent protein (BFP), glutathione-S-transferase (GST), luciferase, horseradish peroxidase NP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein MBP), S-tag, Lex a DNA binding domain (DBD) fusions, GAL4 DNA binding domain fusions, herpes simplex virus ISV) BP16 protein fusions and G-protein fusions (for example G(alpha)16, Gs, Gi). A fusion protein also can be engineered to contain a cleavage site located adjacent to the HM74a.

Preparation of Polynucleotides

A naturally occurring HM74a polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated HM74a polynucleotides. For example, restriction enzymes and probes can be used to isolate polynucleotide fragments which comprise HM74a nucleotide sequences. Isolated polynucleotides are in preparations which are free or at least 70, 80, or 90% free of other molecules.

HM74a cDNA molecules can be made with standard molecular biology techniques, using HM74a mRNA as a template. HM74a cDNA molecules can thereafter be replicated using molecular biology techniques known in the art. An amplification technique, such as PCR, can be used to obtain additional copies of polynucleotides of the invention, using either human genomic DNA or cDNA as a template.

Alternatively, synthetic chemistry techniques can be used to synthesizes HM74a polynucleotides. The degeneracy of the genetic code allows alternate nucleotide sequences to be synthesized which will encode HM74a having, for example, an amino acid sequence shown in SEQ ID NO: 2 or a biologically active variant thereof.

Extending Polynucleotides

Various PCR-based methods can be used to extend nucleic acid sequences encoding human HM74a, for example to detect upstream sequences of HM74a gene such as promoters and regulatory elements. For example, restriction-site PCR uses universal primers to retrieve unknown sequence adjacent to a known locus. Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region. Primers can be designed using commercially available software, such as OLIGO 4.06 Primer Analysis software (National Biosciences Inc., Plymouth, Minn.), to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA. In this method, multiple restriction enzyme digestions and ligations also can be used to place an engineered double-stranded sequence into an unknown fragment of the DNA molecule before performing PCR.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate equipment and software (e.g., GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

HM74a can be obtained, for example, by purification from human cells, by expression of HM74a polynucleotides, or by direct chemical synthesis.

Protein Purification

HM74a can be purified from any human cell which expresses the receptor, including those which have been transfected with expression constructs which express HM74a. A purified HM74a is separated from other compounds which normally associate with HM74a in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis.

Expression of HM74a Polynucleotides

To express HM74a, HM74a polynucleotides can be inserted into an expression vector which contains the necessary elements for the transcription and translation of the inserted coding sequence. Methods which are well known to those skilled in the art can be used to construct expression vectors containing sequences encoding HM74a and appropriate transcriptional and translational control elements. These methods include in vitro recombinant DNA techniques, synthetic techniques, and in vivo genetic recombination.

A variety of expression vector/host systems can be utilized to contain and express sequences encoding HM74a. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding HM74a, vectors based on SV40 or EBV can be used with an appropriate selectable marker.

Bacterial and Yeast Expression Systems

In bacterial systems, a number of expression vectors can be selected. For example, when a large quantity of HM74a is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding HM74a can be ligated into the vector in frame with sequences for the amino-terminal Met and the subsequent 7 residues of β-galactosidase so that a hybrid protein is produced. pIN vectors or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

Plant and Insect Expression Systems

If plant expression vectors are used, the expression of sequences encoding HM74a can be driven by any of a number of promoters. For example, viral promoters such as the 35S and 19S promoters of CaMV can be used alone or in combination with the omega leader sequence from TMV. Alternatively, plant promoters such as the small subunit of RUBISCO or heat shock promoters can be used. These constructs can be introduced into plant cells by direct DNA transformation or by pathogen-mediated transfection.

An insect system also can be used to express HM74a. For example, in one such system *Autographa californica* nuclear polyhedrosis virus (AcNPV) is used as a vector to express foreign genes in *Spodoptera frugiperda* cells or in *Trichoplusia* larvae. Sequences encoding HM74a can be cloned into a non-essential region of the virus, such as the polyhedrin gene, and placed under control of the polyhedrin promoter. Successful insertion of HM74a will render the polyhedrin gene inactive and produce recombinant virus lacking coat protein. The recombinant viruses can then be used to infect *S. frugiperda* cells or *Trichoplusia* larvae in which HM74a can be expressed.

Mammalian Expression Systems

A number of viral-based expression systems can be used to express HM74a in mammalian host cells. For example, if an adenovirus is used as an expression vector, sequences encoding HM74a can be ligated into an adenovirus transcription/-translation complex comprising the late promoter and tripartite leader sequence. Insertion in a non-essential E1 or E3 region of the viral genome can be used to obtain a viable virus which is capable of expressing HM74a in infected host cells [Engelhard, 1994)]. If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles). Specific initiation signals also can be used to achieve more efficient translation of sequences encoding HM74a. Such signals include the ATG initiation codon and adjacent sequences. In cases where sequences encoding HM74a, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic.

Host Cells

A host cell strain can be chosen for its ability to modulate the expression of the inserted sequences or to process the expressed HM74a in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express HM74a can be transformed using expression vectors which can contain viral origins of replication and/or endogenous expression elements and a selectable marker gene on the same or on a separate vector. Following the introduction of the vector, cells can be allowed to grow for 1-2 days in an enriched medium before they are switched to a selective medium. The purpose of the selectable marker is to confer resistance to selection, and its presence allows growth and recovery of cells which successfully express the introduced HM74a sequences. Resistant clones of stably transformed cells can be proliferated using tissue culture techniques appropriate to the cell type. Any number of selection systems can be used to recover transformed cell lines. These include, but are not limited to, the herpes simplex virus thymidine kinase [Logan, (1984)] and adenine phosphoribosyltransferase [Wigler, (1977)] genes which can be employed in tk⁻ or aprt⁻ cells, respectively. Also, antimetabolite, antibiotic, or herbicide resistance can be used as the basis for selection. For example, dhfr confers resistance to methotrexate [Lowy, (1980)], npt confers resistance to the aminoglycosides, neomycin and G-418 [Wigler, (1980)], and als and pat confer resistance to chlorsulfuron and phosphinotricin acetyl-transferase, respectively [Colbere-Garapin, 1981]. Additional selectable genes have been described. For example, trpB allows cells to utilize indole in place of tryptophan, or hisD, which allows cells to utilize histinol in place of histidine. Visible markers such as anthocyanins, β-glucuronidase and its substrate GUS, and luciferase and its substrate luciferin, can be used to identity transformants and to quantify the amount of transient or stable protein expression attributable to a specific vector system Detecting Polypeptide Expression Although the presence of marker gene expression suggests that a HM74a polynucleotide is also present, its presence and expression may need to be confirmed. For example, if a sequence encoding HM74a is inserted within a marker gene sequence, transformed cells containing sequences which encode HM74a can be identified by the absence of marker gene function. Alternatively, a marker gene can be placed in tandem with a sequence encoding HM74a under the control of a single promoter. Expression of the marker gene in response to induction or selection usually indicates expression of HM74a polynucleotide.

Alternatively, host cells which contain a HM74a polynucleotide and which express HM74a can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a polynucleotide sequence encoding HM74a can be detected by DNA-DNA or DNA-RNA hybridization or amplification using probes or fragments or fragments of polynucleotides encoding HM74a. Nucleic acid amplification-based assays involve the use of oligonucleotides selected from sequences encoding HM74a to detect transformants which contain a HM74a polynucleotide.

A variety of protocols for detecting and measuring the expression of HM74a, using either polyclonal or monoclonal antibodies specific for the polypeptide, are known in the art. Examples include enzyme-linked immunosorbent assay (ELISA), radio-immunoassay (RIA), and fluorescence activated cell sorting (FACS). A two-site, monoclonal-based immunoassay using monoclonal antibodies reactive to two non-interfering epitopes on HM74a can be used, or a competitive binding assay can be employed.

A wide variety of labels and conjugation techniques are known by those skilled in the art and can be used in various nucleic acid and amino acid assays. Means for producing labeled hybridization or PCR probes for detecting sequences related to polynucleotides encoding HM74a include oligolabeling, nick translation, end-labeling, or PCR amplification using a labeled nucleotide. Alternatively, sequences encoding HM74a can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with HM74a polynucleotides can be cultured under conditions suitable for the expression and recovery of the protein from cell culture. The poly-peptide produced by a transformed cell can be secreted or contained intracellularly depending on the sequence and/or the vector used. As will be understood by those of skill in the art, expression vectors containing HM74a polynucleotides can be designed to contain signal sequences which direct secretion of soluble HM74a through a prokaryotic or eukaryotic cell membrane or which direct the membrane insertion of membrane-bound HM74a.

As discussed above, other constructions can be used to join a sequence encoding HM74a to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor XA or enterokinase (Invitrogen, San Diego, Calif.) between the purification domain and HM74a also can be used to facilitate purification. One such expression vector provides for expression of a fusion protein containing HM74a and 6 histidine residues preceding a thioredoxin or an enterolinase cleavage site. The histidine residues facilitate purification by IMAC (immobilized metal ion affinity chromatography) Maddox, (1983)], while the enterokinase cleavage site provides a means for purifying HM74a from the fusion protein [Porath, (1992)].

Chemical Synthesis

Sequences encoding HM74a can be synthesized, in whole or in part, using chemical methods well known in the art. Alternatively, HM74a itself can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer). Optionally, fragments of HM74a can be separately synthesized and combined using chemical methods to produce a full-length molecule.

The newly synthesized peptide can be substantially purified by preparative high performance liquid chromatography. The composition of a synthetic HM74a can be confirmed by amino acid analysis or sequencing. Additionally, any portion of the amino acid sequence of HM74a can be altered during direct synthesis and/or combined using chemical methods with sequences from other proteins to produce a variant polypeptide or a fusion protein.

Production of Altered Polypeptides

As will be understood by those of skill in the art, it may be advantageous to produce HM74a polynucleotides possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences referred to herein can be engineered using methods generally known in the art to alter HM74a polynucleotides for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of HM74a.

"Antibody" as used herein includes intact immunoglobulin molecules, as well as fragments thereof, such as Fab, F(ab')$_2$, and Fv, which are capable of binding an epitope of HM74a Typically, at least 6, 8, 10, or 12 contiguous amino acids are required to form an epitope. However, epitopes which involve non-contiguous amino acids may require more, e.g., at least 15, 25, or 50 amino acid. An antibody which specifically binds to an epitope of HM74a can be used therapeutically, as well as in immunochemical assays, such as Western blots, ELISAs, radioimmunoassays, immunohistochemical assays, immunoprecipitations, or other imnunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the HM74a immunogen.

Typically, an antibody which specifically binds to HM74a provides a detection signal at least 5-, 10-, or 20-fold higher than a detection signal provided with other proteins when used in an immunochemical assay. Preferably, antibodies which specifically bind to HM74a do not detect other proteins in immunochemical assays and can immunoprecipitate HM74a from solution.

HM74a can be used to immunize a mammal, such as a mouse, rat, rabbit, guinea pig, monkey, or human, to produce polyclonal antibodies. If desired, HM74a can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g., lysolecithin, pluronic polyols, polyanions, peptides, oil emulsions, keyhole limpet hemocyanin, and dinitrophenol). Among adjuvants used in humans, BCG (*bacilli Calmette-Guerin*) and *Corynebacterium parvum* are especially useful.

Monoclonal antibodies which specifically bind to HM74a can be prepared using any technique which provides for the production of antibody molecules by continuous cell lines in culture. These techniques include, but are not limited to, the hybridoma technique, the human B-cell hybridoma technique, and the EBV-hybridoma technique [Roberge, (1995)].

In addition, techniques developed for the production of "cehimeric antibodies", the splicing of mouse antibody genes to human antibody genes to obtain a molecule with appropriate antigen specificity and biological activity, can be used. Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Antibodies which specifically bind to HM74a can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to HM74a. Antibodies with related specificity, but of distinct idiotypic composition, can be generated by chain shuffling from random combinatorial immunoglobin libraries. Single-chain antibodies also can be constructed using a DNA amplification method, such as PCR, using hybridoma cDNA as a template. Single-chain antibodies can be mono- or bispecific, and can be bivalent or tetravalent. Construction of tetravalent, bispecific single-chain antibodies is taught. A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology.

Antibodies which specifically bind to HM74a also can be produced by inducing in vivo production in the lymphocyte population or by screening immunoglobulin libraries or panels of highly specific binding reagents. Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which HM74a is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of HM74a gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters.

Modifications of HM74a gene expression can be obtained by designing antisense oligonucleotides which will form duplexes to the control, 5', or regulatory regions of the HM74a gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature [Nicholls, (1993)]. An antisense oligonucleotide also can be designed to block translation of mRNA by preventing the transcript from binding to ribosomes.

Precise complementarity is not required for successful complex formation between an antisense oligonucleotide and the complementary sequence of a HM74a polynucleotide. Antisense oligonucleotides which comprise, for example, 2, 3, 4, or 5 or more stretches of contiguous nucleotides which are precisely complementary to a HM74a polynucleotide, each separated by a stretch of contiguous nucleotides which are not complementary to adjacent HM74a nucleotides, can provide sufficient targeting specificity for HM74a mRNA. Preferably, each stretch of complementary contiguous nucleotides is at least 4, 5, 6, 7, or 8 or more nucleotides in length. Noncomplementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular HM74a polynucleotide sequence. Antisense oligonucleotides can be modified without affecting their ability to hybridize to a HM74a polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art.

Ribozymes

Ribozymes are RNA molecules with catalytic activity [Uhlmann, (1987)]. Ribozymes can be used to inhibit gene function by cleaving an RNA sequence, as is known in the art. The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences. The coding sequence of a HM74a polynucleotide can be used to generate ribozymes which will specifically bind to mRNA transcribed from a HM74a polynucleotide. Methods of designing and constructing ribozymes which can cleave other RNA molecules in trans in a highly sequence specific manner have been developed and described in the art. For example, the cleavage activity of ribozymes can be targeted to specific RNAs by engineering a discrete "hybridization" region into the ribozyme. The hybridization region contains a sequence complementary to the target RNA and thus specifically hybridizes with the target RNA.

Specific ribozyme cleavage sites within a HM74a RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate HM74a RNA targets also can be evaluated by testing accessibility to hybridization with complementary oligonucleotides using ribonuclease protection assays. The nucleotide sequences shown in SEQ ID NO: 1 and its complement provide sources of suitable hybridization region sequences. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease HM74a expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells (U.S. Pat. No. 5,641,673). Ribozymes also can be engineered to provide an additional level of regulation, so that destruction of mRNA occurs only when both a ribozyme and a target gene are induced in the cells.

Screening/Screening Assays

Regulators

Regulators as used herein, refer to compounds that affect the activity of a HM74a in vivo and/or in vivo. Regulators can be agonists and antagonists of a HM74a polypeptide and can be compounds that exert their effect on the HM74a activity via the expression, via post-translational modifications or by other means. Agonists of HM74a are molecules which, when bound to HM74a, increase or prolong the activity of HM74a Agonists of HM74a include proteins, nucleic acids, carbohydrates, small molecules, or any other molecule which activate HM74a. Antagonists of HM74a are molecules which, when bound to HM74a, decrease the amount or the duration of the activity of HM74a. Antagonists include proteins, nucleic acids, carbohydrates, antibodies, small molecules, or any other molecule which decrease the activity of HM74a.

The term "modulate", as it appears herein, refers to a change in the activity of HM74a polypeptide. For example, modulation may cause an increase or a decrease in protein activity, binding characteristics, or any other biological, functional, or immunological properties of HM74a.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A" the presence of a polypeptide containing the epitope A, or the presence of free unlabeled A, in a reaction containing free labeled A and the antibody will reduce the amount of labeled A that binds to the antibody.

The invention provides methods (also referred to herein as "screening assays") for identifying compounds which can be used for the treatment of hematological and cardiovascular diseases, disorders of the peripheral and central nervous system, COPD, asthma, genito-urological disorders and inflammation diseases. The methods entail the identification of candidate or test compounds or agents (e.g., peptides,. peptidomimetics, small molecules or other molecules) which bind to HM74a and/or have a stimulatory or inhibitory effect on the biological activity of HM74a or its expression and then determining which of these compounds have an effect on symptoms or diseases regarding the hematological and cardiovascular diseases, disorders of the peripheral and central nervous system, COPD, asthma, genitourological disorders and inflammation diseases in an in vivo assay.

Candidate or test compounds or agents which bind to HM74a and/or have a stimulatory or inhibitory effect on the activity or the expression of HM74a are identified either in assays that employ cells which express HM74a on the cell surface (cell-based assays) or in assays with isolated HM74a (cell-free assays). The various assays can employ a variety of variants of HM74a (e.g., full-length HM74a, a biologically active fragment of HM74a, or a fusion protein which includes all or a portion of HM74a). Moreover, HM74a can be derived from any suitable mammalian species (e.g., human HM74a, rat HM74a or murine HM74a). The assay can be a binding assay entailing direct or indirect measurement of the binding of a test compound or a known HM74a ligand to HM74a. The assay can also be an activity assay entailing direct or indirect measurement of the activity of HM74a. The assay can also be an expression assay entailing direct or indirect measurement of the expression of HM74a mRNA or HM74a protein. The various screening assays are combined with an in vivo assay entailing measuring the effect of the test compound on the symptoms of hematological and cardiovascular diseases, disorders of the peripheral and central nervous system, COPD, asthma, genito-urological disorders and inflammation diseases.

In one embodiment, the invention provides assays for screening candidate or test compounds which bind to or modulate the activity of a membrane-bound (cell surface expressed) form of HM74a. Such assays can employ full-length HM74a, a biologically active fragment of HM74a, or a fusion protein which includes all or a portion of HM74a. As described in greater detail below, the test compound can be obtained by any suitable means, e.g., from conventional compound libraries. Determining the ability of the test compound to bind to a membrane-bound form of HM74a can be accomplished, for example, by coupling the test compound with a radioisotope or enzymatic label such that binding of the test compound to the HM74a expressing cell can be measured by detecting the labeled compound in a complex. For example, the test compound can be labelled with $^{125}$I, $^{35}$S, $^{14}$C, or $^{3}$H, either directly or indirectly, and the radioisotope detected by -direct counting of radio-emmission or by scintillation counting. Alternatively, the test compound can be enzymatically labelled with, for example, horseradish peroxidase, alkaline phosphatase, or luciferase, and the enzymatic label detected by determination of conversion of an appropriate substrate to product.

In a competitive binding format, the assay comprises contacting HM74a expressing cell with a known compound which binds to HM74a to form an assay mixture, contacting the assay mixture with a test compound, and determining the ability of the test compound to interact with the HM74a expressing cell, wherein determining the ability of the test compound to interact with the HM74a expressing cell comprises determining the ability of the test compound to preferentially bind the HM74a expressing cell as compared to the known compound.

In another embodiment, the assay is a cell-based assay comprising contacting a cell expressing a membrane-bound form of HM74a (e.g., full-length HM74a, a biologically active fragment of HM74a, or a fusion protein which includes all or a portion of HM74a) expressed on the cell surface with a test compound and determining the ability of the test compound to modulate (e.g., stimulate or inhibit) the activity of the membrane-bound form of HM74a. Determining the ability of the test compound to modulate the activity of the membrane-bound form of HM74a can be accomplished by any method suitable for measuring the activity of HM74a, e.g., any method suitable for measuring the activity of a G-protein coupled receptor or other seven-transmembrane receptor (described in greater detail below). The activity of a seven-transmembrane receptor can be measured in a number of ways, not all of which are suitable for any given receptor. Among the measures of activity are: alteration in intracellular $Ca^{2+}$ concentration, activation of phospholipase C, alteration in intracellular inositol triphosphate ($IP_3$) concentration, alteration in intracellular diacylglycerol (DAG) concentration, and alteration in intracellular adenosine cyclic 3', 5'-monophosphate (cAMP) concentration.

Determining the ability of the test compound to modulate the activity of HM74a can be accomplished, for example, by determining the ability of HM74a to bind to or interact with a target molecule. The target molecule can be a molecule with which HM74a binds or interacts with in nature, for example, a molecule on the surface of a cell which expresses HM74a, a molecule on the surface of a second cell, a molecule in the extracellular milieu, a molecule associated with the internal surface of a cell membrane or a cytoplasmic molecule. The target molecule can be a component of a signal transduction pathway which facilitates transduction of an extracellular signal (e.g., a signal generated by binding of a HM74a ligand, through the cell membrane and into the cell. The target HM74a molecule can be, for example, a second intracellular protein which has catalytic activity or a protein which facilitates the association of downstream signaling molecules with HM74a.

Determining the ability of HM74a to bind to or interact with a target molecule can be accomplished by one of the methods described above for determining direct binding. In one embodiment, determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, $IP_3$, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response.

The present invention also includes cell-free assays. Such assays involve contacting a form of HM74a (e.g., full-length HM74a, a biologically active fragment of HM74a, or a fusion protein comprising all or a portion of HM74a) with a test compound and determining the ability of the test compound to bind to HM74a. Binding of the test compound to HM74a can be determined either directly or indirectly as described above. In one embodiment, the assay includes contacting HM74a with a known compound which binds HM74a to form an assay mixture, contacting the assay mixture with a test compound, and determining the ability of the test compound to interact with HM74a, wherein determining the ability of the test compound to interact with HM74a comprises determining the ability of the test compound to preferentially bind to HM74a as compared to the known compound.

The cell-free assays of the present invention are amenable to use of either a membrane-bound form of HM74a or a soluble fragment thereof In the case of cell-free assays comprising the membrane-bound form of the polypeptide, it may be desirable to utilize a solubilizing agent such that the membrane-bound form of the polypeptide is maintained in solution. Examples of such solubilizing agents include but are not limited to non-ionic detergents such as n-octylglucoside, n-dodecyl-glucoside, n-dodecylmaltoside, octanoyl-N-methylglucamide, decanoyl-N-methyl-glucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In various embodiments of the above assay methods of the present invention, it may be desirable to immobilize HM74a (or a HM74a target molecule) to facilitate separation of complexed from uncomplexed forms of one or both of the proteins, as well as to accommodate automation of the assay. Binding of a test compound to HM74a, or interaction of HM74a with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase (GST) fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or HM74a, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of HM74a can be determined using standard techniques.

Other techniques for immobilizing proteins on matrices can also be used in the screening assays of the invention. For example, either HM74a or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated plates Pierce Chemical). Alternatively, antibodies reactive with HM74a or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with HM74a or target molecule, as well as enzyme-linked assays which rely on detecting an enzymatic activity associated with HM74a or target molecule.

The screening assay can also involve monitoring the expression of HM74a. For example, regulators of expression of HM74a can be identified in a method in which a cell is contacted with a candidate compound and the expression of HM74a protein or mRNA in the cell is determined. The level of expression of HM74a protein or mRNA the presence of the candidate compound is compared to the level of expression of HM74a protein or mRNA in the absence of the candidate compound. The candidate compound can then be identified as a regulator of expression of HM74a based on this comparison. For example, when expression of HM74a protein or mRNA protein is greater (statistically significantly greater) in the presence of the candidate compound than in its absence, the candidate compound is identified as a stimulator of HM74a protein or mRNA expression. Alternatively, when expression of HM74a protein or mRNA is less (statistically significantly less) in the presence of the candidate compound than in its absence, the candidate compound is identified as an inhibitor of HM74a protein or mRNA expression. The level of HM74a protein or mRNA expression in the cells can be determined by methods described below.

Binding Assays

For binding assays, the test compound is preferably a small molecule which binds to and occupies the active site of HM74a polypeptide, thereby making the ligand binding site inaccessible to substrate such that normal biological activity is prevented. Examples of such small molecules include, but are not limited to, small peptides or peptide-like molecules. Potential ligands which bind to a polypeptide of the invention include, but are not limited to, the natural ligands of known HM74a GPCRs and analogues or derivatives thereof.

In binding assays, either the test compound or the HM74a polypeptide can comprise a detectable label, such as a fluorescent, radioisotopic, chemiluminescent, or enzymatic-label, such as horseradish peroxidase, alkaline phosphatase, or luciferase. Detection of a test compound which is bound to HM74a polypeptide can then be accomplished, for example, by direct counting of radioemmission, by scintillation counting, or by determining conversion of an appropriate substrate to a detectable product. Alternatively, binding of a test compound to a HM74a polypeptide can be determined without labeling either of the interactants. For example, a microphysiometer can be used to detect binding of a test compound with a HM74a polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and HM74a [Haseloff, (1988)].

Determining the ability of a test compound to bind to HM74a also can be accomplished using a technology such as real-time Bimolecular Interaction Analysis (BIA) [McConnell, (1992); Sjolander, (1991)]. BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a HM74a-like polypeptide can be used as a "bait protein" in a two-hybrid assay or three-hybrid assay [Szabo, (1995); U.S. Pat. No. 5,283,317), to identify other proteins which bind to or interact with HM74a and modulate its activity.

The two-hybrid system is based on the modular nature of most transcription factors, which consist of separable DNA-binding and activation domains. Briefly, the assay utilizes two different DNA constructs. For example, in one construct, polynucleotide encoding HM74a can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with HM74a.

It may be desirable to immobilize either the HM74a (or polynucleotide) or the test compound to facilitate separation of the bound form from unbound forms of one or both of the interactants, as well as to accommodate automation of the assay. Thus, either the HM74a-like polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach HM74a-like polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to HM74a (or a polynucleotide encoding for HM74a) can be accomplished in any vessel suitable for containing the reactants. Examples of such vessels include microtiter plates, test tubes, and microcentrifuge tubes.

In one embodiment, HM74a is a fusion protein comprising a domain that allows binding of HM74a to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed HM74a; the mixture is then incubated under conditions conducive to complex formation (e.g. at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either HM74a (or a polynucleotide encoding HM74a) or a test compound can be immobilized utilizing conjugation of biotin and streptavidin. Biotinylated HM74a (or a polynucleotide encoding biotinylated HM74a) or test compounds can be prepared from biotin-NHS (N-hydroxysuccinimide) using techniques well known in the art (e.g., biotinylation kit, Pierce Chemicals, Rockford, Ill.) and immobilized in the wells of streptavidin-coated plates (Pierce Chemical). Alternatively, antibodies which specifically bind to HM74a, polynucleotide, or a test compound, but which do not interfere with a desired binding site, such as the active site of HM74a, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to HM74a polypeptide or test compound, enzyme-linked assays which rely on detecting an activity of HM74a polypeptide, and SDS gel electrophoresis under non-reducing conditions.

Screening for test compounds which bind to a HM74a polypeptide or polynucleotide also can be carried out in an intact cell. Any cell which comprises a HM74a polypeptide or polynucleotide can be used in a cell-based assay system. A HM74a polynucleotide can be naturally occurring in the cell or can be introduced using techniques such as those described above. Binding of the test compound to HM74a or a polynucleotide encoding HM74a is determined as described above.

Functional Assays

Test compounds can be tested for the ability to increase or decrease HM74a activity of a HM74a polypeptide. The HM74a activity can be measured, for example, using methods described in the specific examples, below. HM74a activity can be measured after contacting either a purified HM74a, a cell membrane preparation, or an intact cell with a test compound. A test compound which decreases HM74a activity by at least about 10, preferably about 50, more preferably about 75, 90, or 100% is identified as a potential agent for decreasing HM74a activity. A test compound which increases HM74a activity by at least about 10, preferably about 50, more preferably about 75, 90, or 100% is identified as a potential agent for increasing HM74a activity.

One such screening procedure involves the use of melanophores which are transfected to express HM74a. Such a screening technique is described in PCT WO 92/01810 published Feb. 6, 1992. Thus, for example, such an assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, ie., inhibits activation of the receptor. The screen may be employed for identifying a compound which activates the receptor by contacting such cells with compounds to be screened and determining whether each compound generates a signal, ie., activates the receptor.

Other screening techniques include the use of cells which express HM74a (for example, transfected CHO cells) in a system which measures extracellular pH changes caused by receptor activation [Iwabuchi, (1993)]. For example, compounds may be contacted with a cell which expresses the receptor polypeptide of the present invention and a second messenger response, e.g., signal transduction or pH changes, can be measured to determine whether the potential compound activates or inhibits the receptor. Another such screening technique involves introducing RNA encoding HM74a into *Xenopus* oocytes to transiently express the receptor. The receptor oocytes can then be contacted with the receptor ligand and a compound to be screened, followed by detection of inhibition or activation of a calcium signal in the case of screening for compounds which are thought to inhibit activation of the receptor.

Another screening technique involves expressing HM74a in cells in which the receptor is linked to a phospholipase C or D. Such cells include endothelial cells, smooth muscle cells, embryonic kidney cells, etc. The screening may be accomplished as described above by quantifying the degree of activation of the receptor from changes in the phospholipase activity.

Gene Expression

In another embodiment, test compounds which increase or decrease HM74a gene expression are identified. As used herein, the term "correlates with expression of a polynucleotide" indicates that the detection of the presence of nucleic acids, the same or related to a nucleic acid sequence encoding HM74a, by northern analysis or relatime PCR is indicative of the presence of nucleic acids encoding HM74a in a sample, and thereby correlates with expression of the transcript from the polynucleotide encoding HM74a. The term "microarray", as used herein, refers to an array of distinct polynucleotides or oligonucleotides arrayed on a substrate, such as paper, nylon or any other type of membrane, filter, chip, glass slide, or any other suitable solid support. A HM74a polynucleotide is contacted with a test compound, and the expression of an RNA or polypeptide product of HM74a polynucleotide is determined. The level of expression of appropriate mRNA or polypeptide in the presence of the test compound is compared to the level of expression of mRNA or polypeptide in the absence of the test compound. The test compound can then be identified as a regulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of HM74a mRNA or polypeptide expression in the cells can be determined by methods well known in the art for detecting mRNA or polypeptide. Either qualitative or quantitative methods can be used. The presence of polypeptide products of HM74a polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labelled amino acids into HM74a.

Such screening can be carried out either in a cell-free assay system or in an intact cell. Any cell which expresses HM74a polynucleotide can be used in a cell-based assay system. The HM74a polynucleotide can be naturally occurring in the cell or can be introduced using techniques such as those described above. Either a primary culture or an established cell line can be used.

Test Compounds

Suitable test compounds for use in the screening assays of the invention can be obtained from any suitable source, e.g., conventional compound libraries. The test compounds can also be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds [Lam, (1997)]. Examples of methods for the synthesis of molecular libraries can be found in the art. Libraries of compounds may be presented in solution or on beads, bacteria, spores, plasmids or phage.

Modeling of Regulators

Computer modeling and searching technologies permit identification of compounds, or the improvement of already identified compounds, that can modulate HM74a expression or activity. Having identified such a compound or composition, the active sites or regions are identified. Such active sites might typically be ligand binding sites, such as the interaction domain of the ligand with HM74a. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential HM74a modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Therapeutic Indications and Methods

It was found by the present applicant that HM74a is expressed in various human tissues.

Neurology

CNS disorders include disorders of the central nervous system as well as disorders of the peripheral nervous system.

CNS disorders include, but are not limited to brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, and Korsakoff's psychosis, within the meaning of the definition are also considered to be CNS disorders. Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be CNS disorders. Pain, within the meaning of this definition, is also considered to be a CNS disorder. Pain can be associated with CNS disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, phantom feeling, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and postherpetic neuralgia. Pain associated with peripheral nerve damage, central pain (i.e. due to cerebral ischemia) and various chronic pain i.e., lumbago, back pain (low back pain), inflammatory and/or rheumatic pain. Headache pain (for example, migraine with aura, migraine without aura, and other migraine disorders), episodic and chronic tension-type headache, tension-type like headache, cluster headache, and chronic paroxysmal hemicrania are also CNS disorders.

Visceral pain such as pancreatits, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome and protatodynia are also CNS disorders.

Also considered to be a disorder of the nervous system are acute pain, for example postoperative pain, and pain after trauma.

The human HM74a is highly expressed in the following brain tissues: brain, Alzheimer brain, cerebellum (right), cerebellum (left), cerebral cortex, Alzheimer brain frontal lobe, occipital lobe, pons, substantia nigra, cerebral meninges, corpus callosum, dorsal root ganglia, neuroblastoma IMR32 cells. The expression in brain tissues and in particular the differential expression between diseased tissue Alzheimer brain and healthy tissue brain, between diseased tissue Alzheimer brain frontal lobe and healthy tissue frontal lobe demonstrates that the human HM74a or mRNA can be utilized to diagnose nervous system diseases. Additionally the activity of the human HM74a can be modulated to treat nervous system diseases.

Cardiovascular Disorders

Heart failure is defined as a pathophysiological state in which an abnormality of cardiac function is responsible for the failure of the heart to pump blood at a rate commensurate with the requirement of the metabolizing tissue. It includes all forms of pumping failures such as high-output and low-output, acute and chronic, right-sided or left-sided, systolic or diastolic, independent of the underlying cause.

Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included as well as the acute treatment of MI and the prevention of complications.

Ischemic diseases are conditions in which the coronary flow is restricted resulting in a perfusion which is inadequate to meet the myocardial requirement for oxygen. This group of diseases includes stable angina, unstable angina and asymptomatic ischemia.

Arrhythmias include all forms of atrial and ventricular tachyarrhythmias, atrial tachycardia, atrial flutter, atrial fibrillation, atrio-ventricular reentrant tachycardia, preexitation syndrome, ventricular tachycardia, ventricular flutter, ventricular fibrillation, as well as bradycardic forms of arrhythmias.

Hypertensive vascular diseases include primary as well as all kinds of secondary arterial hypertension, renal, endocrine, neurogenic, others. The genes may be used as drug targets for the treatment of hypertension as well as for the prevention of all complications arising from cardiovascular diseases.

Peripheral vascular diseases are defined as vascular diseases in which arterial and/or venous flow is reduced resulting in an imbalance between blood supply and tissue oxygen demand. It includes chronic peripheral arterial occlusive disease (PAOD), acute arterial thrombosis and embolism, inflammatory vascular disorders, Raynaud's phenomenon and venous disorders.

Atherosclerosis is a cardiovascular disease in which the vessel wall is remodeled, compromising the lumen of the vessel. The atherosclerotic remodeling process involves accumulation of cells, both smooth muscle cells and monocyte/macrophage inflammatory cells, in the intima of the vessel wall. These cells take up lipid, likely from the circulation, to form a mature atherosclerotic lesion. Although the formation of these lesions is a chronic process, occurring over decades of an adult human life, the majority of the morbidity associated with atherosclerosis occurs when a lesion ruptures, releasing thrombogenic debris that rapidly occludes the artery. When such an acute event occurs in the coronary artery, myocardial infarction can ensue, and in the worst case, can result in death.

The formation of the atherosclerotic lesion can be considered to occur in five overlapping stages such as migration, lipid accumulation, recruitment of inflammatory cells, proliferation of vascular smooth muscle cells, and extracellular matrix deposition. Each of these processes can be shown to occur in man and in animal models of atherosclerosis, but the relative contribution of each to the pathology and clinical significance of the lesion is unclear.

Thus, a need exists for therapeutic methods and agents to treat cardiovascular pathologies, such as atherosclerosis and other conditions related to coronary artery disease.

Cardiovascular diseases include but are not limited to disorders of the heart and the vascular system like congestive heart failure, myocardial infarction, ischemic diseases of the heart, all kinds of atrial and ventricular arrhythmias, hypertensive vascular diseases, peripheral vascular diseases, and atherosclerosis.

Too high or too low levels of fats in the bloodstream, especially cholesterol, can cause long-term problems. The risk to develop atherosclerosis and coronary artery or carotid artery disease (and thus the risk of having a heart attack or stroke) increases with the total cholesterol level increasing. Nevertheless, extremely low cholesterol levels may not be healthy. Examples of disorders of lipid metabolism are hyperlipidemia (abnormally high levels of fats (cholesterol, triglycerides, or both) in the blood, may be caused by family history of hyperlipidemia), obesity, a high-fat diet, lack of exercise, moderate to high alcohol consumption, cigarette smoking, poorly controlled diabetes, and an underactive thyroid gland), hereditary hyperlipidemias (type I hyperlipoproteinemia (familial hyperchylomicronemia), type II hyperlipoproteinemia (familial hypercholesterolemia), type In hyperlipoproteinemia, type IV hyperlipoproteinemia, or type V hyperlipoproteinemia), hypolipoproteinemia, lipidoses (caused by abnormalities in the enzymes that metabolize fats), Gaucher's disease, Niemann-Pick disease, Fabry's disease, Wolman's disease, cerebrotendinous xanthomatosis, sitosterolemia, Refsum's disease, or Tay-Sachs disease.

Kidney disorders may lead to hypertension or hypotension. Examples for kidney problems possibly leading to hypertension are renal artery stenosis, pyelonephritis, glomerulonephritis, kidney tumors, polycistic kidney disease, injury to the kidney, or radiation therapy affecting the kidney. Excessive urination may lead to hypotension.

The human HM74a is highly expressed in the following cardiovascular related tissues: heart, pericardium, heart atrium (right), heart atrium (left), artery, coronary artery, coronary artery sclerotic. Expression in the above mentioned tissues and in particular the differential expression between diseased tissue coronary artery sclerotic and healthy tissue coronary artery demonstrates that the human HM74a or mRNA can be utilized to diagnose of cardiovascular diseases. Additionally the activity of the human HM74a can be modulated to treat cardiovascular diseases.

Hematological Disorders

Hematological disorders comprise diseases of the blood and all its constituents as well as diseases of organs and tissues involved in the generation or degradation of all the constituents of the blood. They include but are not limited to 1) Anemias, 2) Myeloproliferative Disorders, 3) Hemorrhagic Disorders, 4) Leukopenia, 5) Eosinophilic Disorders, 6) Leukemias, 7) Lymphomas, 8) Plasma Cell Dyscrasias, 9) Disorders of the Spleen in the course of hematological disorders. Disorders according to 1) include, but are not limited to anemias due to defective or deficient hem synthesis, deficient erythropoiesis. Disorders according to 2) include, but are not limited to polycythemia vera, tumor-associated erythrocytosis, myelofibrosis, thrombocythemia. Disorders according to 3) include, but are not limited to vasculitis, thrombocytopenia, heparin-induced thrombocytopenia, thrombotic thrombocytopenic purpura, hemolytic-uremic syndrome, hereditary and acquired disorders of platelet function, hereditary coagulation disorders. Disorders according to 4) include, but are not limited to neutropenia, lymphocytopenia. Disorders according to 5) include, but are not limited to hypereosinophilia, idiopathic hypereosinophilic syndrome. Disorders according to 6) include, but are not limited to acute myeloic leukemia, acute lymphoblastic leukemia, chronic myelocytic leukemia, chronic lymphocytic leukemia, myelodysplastic syndrome. Disorders according to 7) include, but are not limited to Hodgkin's disease, non-Hodgkin's lymphoma, Burkitt's lymphoma, mycosis fungoides cutaneous T-cell lymphoma. Disorders according to 8) include, but are not limited to multiple myeloma, macroglobulinemia, heavy chain diseases. In extension of the preceding idiopathic thrombocytopenic purpura, iron deficiency anemia, megaloblastic anemia (vitamin B12 deficiency), aplastic anemia, thalassemia, malignant lymphoma bone marrow invasion, malignant lymphoma skin invasion, hemolytic uremic syndrome, giant platelet disease are considered to be hematological diseases too.

The human HM74a is highly expressed in the following tissues of the hematological system: leukocytes peripheral blood), bone marrow, erythrocytes, lymphnode, thymus, thrombocytes, bone marrow CD34+ cells, bone marrow CD15+ cells, spleen, spleen liver cirrhosis. The expression in the above mentioned tissues and in particular the differential expression between diseased tissue spleen liver cirrhosis and healthy tissue spleen demonstrates that the human HM74a or mRNA can be utilized to diagnose of hematological diseases. Additionally the activity of the human HM74a can be modulated to treat hematological disorders.

Gastrointestinal and Liver Diseases

Gastrointestinal diseases comprise primary or secondary, acute or chronic diseases of the organs of the gastrointestinal tract which may be acquired or inherited, benign or malignant or metaplastic, and which may affect the organs of the gastrointestinal tract or the body as a whole. They comprise but are not limited to 1) disorders of the esophagus like achalasia, vigoruos achalasia, dysphagia, cricopharyngeal incoordination, pre-esophageal dysphagia, diffuse esophageal spasm, globus sensation, Barrett's metaplasia, gastroesophageal reflux, 2) disorders of the stomach and duodenum like functional dyspepsia, inflammation of the gastric mucosa, gastritis, stress gastritis, chronic erosive gastritis, atrophy of gastric glands, metaplasia of gastric tissues, gastric ulcers, duodenal ulcers, neoplasms of the stomach, 3) disorders of the pancreas like acute or chronic pancreatitis, insufficiency of the exocrinic or endocrinic tissues of the pancreas like steatorrhea, diabetes, neoplasms of the exocrine or endocrine pancreas like 3.1) multiple endocrine neoplasia syndrome, ductal adenocarcinoma, cystadenocarcinoma, islet cell tumors, insulinoma, gastrinoma, carcinoid tumors, glucagonoma, Zollinger-Ellison syndrome, Vipoma syndrome, malabsorption syndrome, 4) disorders of the bowel like chronic inflammatory diseases of the bowel, Crohn's disease, ileus, diarrhea and constipation, colonic inertia, megacolon, malabsorption syndrome, ulcerative colitis, 4.1) functional bowel disorders like irritable bowel syndrome, 4.2) neoplasms of the bowel like familial polyposis, adenocarcinoma, primary malignant lymphoma, carcinoid tumors, Kaposi's sarcoma, polyps, cancer of the colon and rectum.

Liver diseases comprise primary or secondary, acute or chronic diseases or injury of the liver which may be acquired or inherited, benign or malignant, and which may affect the liver or the body as a whole. They comprise but are not limited to disorders of the bilirubin metabolism, jaundice, syndroms of Gilbert's, Crigler-Najjar, Dubin-Johnson and Rotor; intrahepatic cholestasis, hepatomegaly, portal hypertension, ascites, Budd-Chiari syndrome, portal-systemic encephalopathy, fatty liver, steatosis, Reye's syndrome, liver diseases due to alcohol, alcoholic hepatitis or cirrhosis, fibrosis and cirrhosis, fibrosis and cirrhosis of the liver due to inborn errors of metabolism or exogenous substances, storage diseases, syndromes of Gaucher's, Zellweger's, Wilson's—disease, acute or chronic hepatitis, viral hepatitis and its variants, inflammatory conditions of the liver due to viruses, bacteria, fungi, protozoa, helminths; drug induced disorders of the liver, chronic liver diseases like primary sclerosing cholangitis, alpha$_1$-antitrypsin-deficiency, primary biliary cirrhosis, postoperative liver disorders like postoperative intrahepatic cholestasis, hepatic granulomas, vascular liver disorders associated with systemic disease, benign or malignant neoplasms of the liver, disturbance of liver metabolism in the new-born or prematurely born.

The human HM74a is highly expressed in the following tissues of the gastro-enterological system: esophagus, esophagus tumor, stomach tumor, rectum. The expression in the above mentioned tissues and in particular the differential expression between diseased tissue esophagus tumor and healthy tissue esophagus, between diseased tissue stomach tumor and healthy tissue stomach demonstrates that the human HM74a or mRNA can be utilized to diagnose of gastroenterological disorders. Additionally the activity of the human HM74a can be modulated to treat gastroenterological disorders.

Cancer Disorders

Cancer disorders within the scope of this definition comprise any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. Cells and tissues are cancerous when they grow more rapidly than normal cells, displacing or spreading into the surrounding healthy tissue or any other tissues of the body described as metastatic growth, assume abnormal shapes and sizes, show changes in their nucleocytoplasmatic ratio, nuclear polychromasia, and finally may cease. Cancerous cells and tissues may affect the body as a whole when causing paraneoplastic syndromes or if cancer occurs within a vital organ or tissue, normal function will be impaired or halted, with possible fatal results. The ultimate involvement of a vital organ by cancer, either primary or metastatic, may lead to the death of the mammal affected. Cancer tends to spread, and the extent of its spread is usually related to an individual's chances of surviving the disease. Cancers are generally said to be in one of three stages of growth: early, or localized, when a tumor is still confined to the tissue of origin, or primary site; direct extension, where cancer cells from the tumour have invaded adjacent tissue or have spread only to regional lymph nodes; or metastasis, in which cancer cells have migrated to distant parts of the body from the primary site, via the blood or lymph systems, and have established secondary sites of infection. Cancer is said to be malignant because of its tendency to cause death if not treated. Benign tumors usually do not cause death, although they may if they interfere with a normal body function by virtue of their location, size, or paraneoplastic side effects. Hence benign tumors fall under the definition of cancer within the scope of this definition as well. In general, cancer cells divide at a higher rate than do normal cells, but the distinction between the growth of cancerous and normal tissues is not so much the rapidity of cell division in the former as it is the partial or complete loss of growth restraint in cancer cells and their failure to differentiate into a useful, limited tissue of the type that characterizes the functional equilibrium of growth of normal tissue. Cancer tissues may express certain molecular receptors and probably are influenced by the host's susceptibility and immunity and it is known that certain cancers of the breast and prostate, for example, are considered dependent on specific hormones for their existence. The term "cancer" under the scope of the definition is not limited to simple benign neoplasia but comprises any other benign and malign neoplasia like 1) Carcinoma, 2) Sarcoma, 3) Carcinosarcoma, 4) Cancers of the blood-forming tissues, 5) tumors of nerve tissues including the brain, 6) cancer of skin cells.

Cancer according to 1) occurs in epithelial tissues, which cover the outer body (the skin) and line mucous membranes and the inner cavitary structures of organs e.g. such as the breast, lung, the respiratory and gastrointestinal tracts, the endocrine glands, and the genitourinary system. Ductal or glandular elements may persist in epithelial tumors, as in adenocarcinomas like e.g. thyroid adenocarcinoma, gastric adenocarcinoma, uterine adenocarcinoma Cancers of the pavement-cell epithelium of the skin and of certain mucous membranes, such as e.g. cancers of the tongue, lip, larynx, urinary bladder, uterine cervix, or penis, may be termed epidermoid or squamous-cell carcinomas of the respective tissues and are in the scope of the definition of cancer as well. Cancer according to 2) develops in connective tissues, including fibrous tissues, adipose (fat) tissues, muscle, blood vessels, bone, and cartilage like e.g. osteogenic sarcoma; liposarcoma, fibrosarcoma, synovial sarcoma. Cancer according to 3) is cancer that develops in both epithelial and connective tissue. Cancer disease within the scope of this definition may be primary or secondary, whereby primary indicates that the cancer originated in the tissue where it is found rather than was established as a secondary site through metastasis from another lesion. Cancers and tumor diseases within the scope of this definition may be benign or malign and may affect all anatomical structures of the body of a mammal. By example but not limited to they comprise cancers and tumor diseases of I) the bone marrow and bone marrow derived cells (leukemias), II) the endocrine and exocrine glands like e.g. thyroid, parathyroid, pituitary, adrenal glands, salivary glands, pancreas III) the breast, like e.g. benign or malignant tumors in the mammary glands of either a male or a female, the mammary ducts, adenocarcinoma, medullary carcinoma, comedo carcinoma, Paget's disease of the nipple, inflammatory carcinoma of the young woman, IV) the lung, V) the stomach, VI) the liver and spleen, VII) the small intestine, VIII) the colon, IX) the bone and its supportive and connective tissues like malignant or benign bone tumour, e.g. malignant osteogenic sarcoma, benign osteoma, cartilage tumors; like malignant chondrosarcoma or benign chondroma; bone marrow tumors like malignant myeloma or benign eosinophilic granuloma, as well as metastatic tumors from bone tissues at other locations of the body; X) the mouth, throat, larynx, and the esophagus, XI) the urinary bladder and the internal and external organs and structures of the urogenital system of male and female like ovaries, uterus, cervix of the uterus, testes, and prostate gland, XII) the prostate, XIII) the pancreas, like ductal carcinoma of the pancreas; XIV) the lymphatic tissue like lymphomas and other tumors of lymphoid origin, XV) the skin, XVI) cancers and tumor diseases of all anatomical structures belonging to the respiration and respiratory systems including thoracal muscles and linings, XVII) primary or secondary cancer of the lymph nodes XVIII) the tongue and of the bony structures of the hard palate or sinuses, XVIV) the mouth, cheeks, neck and salivary glands, XX) the blood vessels including the heart and their linings, XXI) the smooth or skeletal muscles and their ligaments and linings, XXII the peripheral, the autonomous, the central nervous system including the cerebellum, XXIII) the adipose tissue.

The human HM74a is highly expressed in the following cancer tissues: esophagus tumor, stomach tumor, lung tumor, ovary tumor, kidney tumor. The expression in the above mentioned tissues and in particular the differential expression between diseased tissue esophagus tumor and healthy tissue esophagus, between diseased tissue stomach tumor and healthy tissue stomach, between diseased tissue lung tumor and healthy tissue lung, between diseased tissue ovary tumor and healthy tissue ovary, between diseased tissue kidney tumor and healthy tissue kidney demonstrates that the human HM74a or mRNA can be utilized to diagnose of cancer. Additionally the activity of the human HM74a can be modulated to treat cancer.

Inflammatory Diseases

Inflammatory diseases comprise diseases triggered by cellular or non-cellular mediators of the immune system or tissues causing the inflammation of body tissues and subsequently producing an acute or chronic inflammatory condition. Examples for such inflammatory diseases are hypersensitivity reactions of type I-IV, for example but not limited to hypersensitivity diseases of the lung including asthma, atopic diseases, allergic rhinitis or conjunctivitis, angioedema of the lids, hereditary angioedema, antireceptor hypersensitivity reactions and autoimmune diseases, Hashimoto's thyroiditis, systemic lupus erythematosus, Goodpasture's syndrome, pemphigus, myasthenia gravis, Grave's and Raynaud's disease, type B insulin-resistant diabetes, rheumatoid arthritis, psoriasis, Crohn's disease, scleroderma, mixed connective tissue disease, polymyositis, sarcoidosis, glomerulonephritis, acute or chronic host versus graft reactions.

The human HM74a is highly expressed in the following tissues of the immune system and tissues responsive to components of the immune system as well as in the following tissues responsive to mediators of inflammation: leukocytes (peripheral blood), bone marrow, bone marrow CD15+ cells, spleen liver cirrhosis, lung COPD. The expression in the above mentioned tissues and in particular the differential expression between diseased tissue spleen liver cirrhosis and healthy tissue spleen, between diseased tissue lung COPD and healthy tissue lung demonstrates that the human HM74a or mRNA can be utilized to diagnose of inflammatory diseases. Additionally the activity of the human HM74a can be modulated to treat inflammatory diseases.

Disorders Related to Pulmology

Asthma is thought to arise as a result of interactions between multiple genetic and environmental factors and is characterized by three major features: 1) intermittent and reversible airway obstruction caused by bronchoconstriction, increased mucus production, and thickening of the walls of the airways that leads to a narrowing of the airways, 2) airway hyperresponsiveness, and 3) airway inflammation. Certain cells are critical to the inflammatory reaction of asthma and they include T cells and antigen presenting cells, B cells that produce IgE, and mast cells, basophils, eosinophils, and other cells that bind IgE. These effector cells accumulate at the site of allergic reaction in the airways and release toxic products that contribute to the acute pathology and eventually to tissue destruction related to the disorder. Other resident cells, such as smooth muscle cells, lung epithelial cells, mucus-producing cells, and nerve cells may also be abnormal in individuals with asthma and may contribute to its pathology. While the airway obstruction of asthma, presenting clinically as an intermittent wheeze and shortness of breath, is generally the most pressing symptom of the disease requiring immediate treatment, the inflammation and tissue destruction associated with the disease can lead to irreversible changes that eventually make asthma a chronic and disabling disorder requiring long-term management.

Chronic obstructive pulnonary (or airways) disease (COPD) is a condition defined physiologically as airflow obstruction that generally results from a mixture of emphysema and peripheral airway obstruction due to chronic bronchitis [Botstein, 1980]. Emphysema is characterised by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does also occur in non-smokers.

The human HM74a is highly expressed in the following tissues of the respiratory system: leukocytes (peripheral blood), bone marrow CD15+ cells, lung, lung right upper lobe, lung right mid lobe, lung right lower lobe, lung tumor, lung COPD, trachea. The expression in the above mentioned tissues and in particular the differential expression between diseased tissue lung tumor and healthy tissue lung, between diseased tissue lung COPD and healthy tissue lung demonstrates that the human HM74a or mRNA can be utilized to diagnose of respiratory diseases. Additionally the activity of the human HM74a can be modulated to treat those diseases.

Disorders Related to Urology

Genitourinary disorders comprise benign and malign disorders of the organs constituting the genitourinary system of female and male, renal diseases like acute or chronic renal failure, immunologically mediated renal diseases like renal transplant rejection, lupus nephritis, immune complex renal diseases, glomerulopathies, nephritis, toxic nephropathy, obstructive uropathies like benign prostatic hyperplasia (BPH), neurogenic bladder syndrome, urinary incontinence like urge-, stress-, or overflow incontinence, pelvic pain, and erectile dysfunction.

The human HM74a is highly expressed in the following urological tissues: ureter, penis, corpus cavernosum, fetal kidney, kidney, kidney tumor. The expression in the above mentioned tissues and in particular the differential expression between diseased tissue kidney tumor and healthy tissue kidney demonstrates that the human HM74a or mRNA can be utilized to diagnose of urological disorders. Additionally the activity of the human HM74a can be modulated to treat urological disorders.

Applications

The present invention provides for both prophylactic and therapeutic methods for disorders of the peripheral and central nervous system, cardiovascular diseases, hematological diseases, cancer, inflammation, urological diseases, respiratory diseases and gastroenterological diseases.

The regulatory method of the invention involves contacting a cell with an agent that modulates one or more of the activities of HM74a. An agent that modulates activity can be an agent as described herein, such as a nucleic acid or a protein, a naturally-occurring cognate ligand of the polypeptide, a peptide, a peptidomimetic, or any small molecule. In one embodiment, the agent stimulates one or more of the biological activities of HM74a. Examples of such stimulatory agents include the active HM74a and nucleic acid molecules encoding a portion of HM74a. In another embodiment, the agent inhibits one or more of the biological activities of HM74a. Examples of such inhibitory agents include antisense nucleic acid molecules and antibodies. These regulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by unwanted expression or activity of HM74a or a protein in the HM74a signaling pathway. In one embodiment, the method involves administering an agent like any agent identified or being identifiable by a screening assay as described herein, or combination of such agents that modulate say upregulate or downregulate the expression or activity of HM74a or of any protein in the HM74a signaling pathway. In another embodiment, the method involves administering a regulator of HM74a as therapy to compensate for reduced or undesirably low expression or activity of HM74a or a protein in the HM74a signaling pathway.

Stimulation of activity or expression of HM74a is desirable in situations in which activity or expression is abnormally low and in which increased activity is likely to have a beneficial effect. Conversely, inhibition of activity or expression of HM74a is desirable in situations in which activity or expression of HM74a is abnormally high and in which decreasing its activity is likely to have a beneficial effect.

This invention is further illustrated by the following examples which should not be construed as limiting. The contents of all references, patents and published patent applications cited throughout this application are hereby incorporated by reference.

Pharmaceutical Compositions

This invention further pertains to novel agents identified by the above-described screening assays and uses thereof for treatments as described herein.

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes pharmaceutical compositions comprising a regulator of HM74a expression or activity (and/or a regulator of the activity or expression of a protein in the HM74a signaling pathway) as well as methods for preparing such compositions by combining one or more such regulators and a pharmaceutically acceptable carrier. Also within the invention are pharmaceutical compositions comprising a regulator identified using the screening assays of the invention packaged with instructions for use. For regulators that are antagonists of HM74a activity or which reduce HM74a expression, the instructions would specify use of the pharmaceutical composition for treatment of hematological and cardiovascular diseases, disorders of the peripheral and central nervous system, COPD, asthma, genito-urological disorders and inflammation diseases. For regulators that are agonists of HM74a activity or increase HM74a expression, the instructions would specify use of the pharmaceutical composition for treatment of hematological and cardiovascular diseases, disorders of the peripheral and central nervous system, COPD, asthma, genito-urological disorders and inflammation diseases.

An antagonist of HM74a may be produced using methods which are generally known in the art. In particular, purified HM74a may be used to produce antibodies or to screen libraries of pharmaceutical agents to identify those which specifically bind HM74a. Antibodies to HM74a may also be generated using methods that are well known in the art. Such antibodies may include, but are not limited to, polyclonal, monoclonal, chimeric, single chain antibodies, Fab fragments, and fragments produced by a Fab expression library. Neutralizing antibodies like those which inhibit dimer formation are especially preferred for therapeutic use.

In another embodiment of the invention, the polynucleotides encoding HM74a, or any fragment or complement thereof, may be used for therapeutic purposes. In one aspect, the complement of the polynucleotide encoding HM74a may be used in situations in which it would be desirable to block the transcription of the mRNA. In particular, cells may be transformed with sequences complementary to polynucleotides encoding HM74a. Thus, complementary molecules or fragments may be used to modulate HM74a activity, or to achieve regulation of gene function. Such technology is now well known in the art, and sense or antisense oligonucleotides or larger fragments can be designed from various locations along the coding or control regions of sequences encoding HM74a.

Expression vectors derived from retroviruses, adenoviruses, or herpes or vaccina viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding HM74a. These techniques are described, for example, in [Scott and Smith (1990) Science 249: 386-390].

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition containing HM74a in conjunction with a pharmaceutically acceptable carrier, for any of the therapeutic effects discussed above. Such pharmaceutical compositions may consist of HM74a, antibodies to HM74a, and mimetics, agonists, antagonists, or inhibitors of HM74a. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin. Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration. For pharmaceutical compositions which include an antagonist of HM74a activity, a compound which reduces expression of HM74a, or a compound which reduces expression or activity of a protein in the HM74a signaling pathway or any combination thereof, the instructions for administration will specify use of the composition for hematological and cardiovascular diseases, disorders of the peripheral and central nervous system, COPD, asthma, genito-urological disorders and inflammation diseases. For pharmaceutical compositions which include an agonist of HM74a activity, a compound which increases expression of HM74a, or a compound which increases expression or activity of a protein in the HM74a signaling pathway or any combination thereof, the instructions for administration will specify use of the composition for hematological and cardiovascular diseases, disorders of the peripheral and central nervous system, COPD, asthma, genito-urological disorders and inflammation diseases.

Diagnostics

In another embodiment, antibodies which specifically bind HM74a may be used for the diagnosis of disorders characterized by the expression of HM74a, or in assays to monitor patients being treated with HM74a or agonists, antagonists, and inhibitors of HM74a. Antibodies useful for diagnostic purposes may be prepared in the same manner as those described above for therapeutics. Diagnostic assays for HM74a include methods which utilize the antibody and a label to detect HM74a in human body fluids or in extracts of cells or tissues. The antibodies may be used with or without modification, and may be labeled by covalent or non-covalent joining with a reporter molecule. A wide variety of reporter molecules, several of which are described above, are known in the art and may be used.

A variety of protocols for measuring HM74a, including ELISAs, RIAs, and FACS, are known in the art and provide a basis for diagnosing altered or abnormal levels of HM74a expression. Normal or standard values for HM74a expression are established by combining body fluids or cell extracts taken from normal mammalian subjects, preferably human, with antibody to HM74a under conditions suitable for complex formation The amount of standard complex formation may be quantified by various methods, preferably by photometric means. Quantities of HM74a expressed in subject samples from biopsied tissues are compared with the standard values. Deviation between standard and subject values establishes the parameters for diagnosing disease.

In another embodiment of the invention, the polynucleotides encoding HM74a may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HM74a may be correlated with disease. The diagnostic assay may be used to distinguish between absence, presence, and excess expression of HM74a, and to monitor regulation of HM74a levels during therapeutic intervention.

Polynucleotide sequences encoding HM74a may be used for the diagnosis of disorders of the peripheral and central nervous system, cardiovascular diseases, hematological diseases, cancer, inflammation, urological diseases, respiratory diseases and gastroenterological diseases associated with expression of HM74a. The polynucleotide sequences encoding HM74a may be used in Southern, Northern, or dot-blot analysis, or other membrane-based technologies; in PCR technologies; in dipstick, pin, and ELISA assays; and in microarrays utilizing fluids or tissues from patient biopsies to detect altered HM74a expression. Such qualitative or quantitative methods are well known in the art.

In a particular aspect, the nucleotide sequences encoding HM74a may be useful in assays that detect the presence of associated disorders, particularly those mentioned above. The nucleotide sequences encoding HM74a may be labelled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding HM74a in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of disorders of the peripheral and central nervous system, cardiovascular diseases, hematological diseases, cancer, inflammation, urological diseases, respiratory diseases and gastroenterological diseases associated with expression of HM74a, a normal or standard profile for expression is established. This may be accomplished by combining body fluids or cell extracts taken from normal subjects, either animal or human, with a sequence, or a fragment thereof, encoding HM74a, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Another technique for drug screening which may be used provides for high throughput screening of compounds having suitable binding affinity to the protein of interest as described in published PCT application WO84/03564. In this method, large numbers of different small test compounds are synthesized on a solid substrate, such as plastic pins or some other surface. The test compounds are reacted with HM74a, or fragments thereof, and washed. Bound HM74a is then detected by methods well known in the art. Purified HM74a can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HM74a specifically compete with a test compound for binding HM74a. In this manner, antibodies can be used to detect the presence of any peptide which shares one or more antigenic determinants with HM74a.

G-protein coupled receptors are ubiquitous in the mammalian host and are responsible for many biological functions, including many pathologies. Accordingly, it is desirable to find compounds and drugs which stimulate a G-protein coupled receptor on the one hand and which can inhibit the function of a G-protein coupled receptor on the other hand. For example, compounds which activate the G-protein coupled receptor may be employed for therapeutic purposes, such as the treatment of asthma, Parkinson's disease, acute heart failure, urinary retention, and osteoporosis. In particular, compounds which activate the receptors of the present invention are useful in treating various cardiovascular ailments such as caused by the lack of pulmonary blood flow or hypertension. In addition these compounds may also be used in treating various physiological disorders relating to abnormal control of fluid and electrolyte homeostasis and in diseases associated with abnormal angiotensin-induced aldosterone secretion.

In general, compounds which inhibit activation of the G-protein coupled receptor may be employed for a variety of therapeutic purposes, for example, for the treatment of hypotension and/or hypertension, angina pectoris, myocardial infarction, ulcers, asthma, allergies, benign prostatic hypertrophy, and psychotic and neurological disorders including schizophrenia, manic excitement, depression, delirium, dementia or severe mental retardation, dyskinesias, such as Huntington's disease or Tourett's syndrome, among others. Compounds which inhibit G-protein coupled receptors have also been useful in reversing endogenous anorexia and in the control of bulimia.

Determination of a Therapeutically Effective Dose

The determination of a therapeutically effective dose is well within the capability of those skilled in the art. A therapeutically effective dose refers to that amount of active ingredient which increases or decreases HM74a activity relative to HM74a activity which occurs in the absence of the therapeutically effective dose. For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 micrograms to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. If the reagent is a single-chain antibody, polynucleotides encoding the antibody can be constructed and introduced into a cell either ex vivo or in vivo using well-established techniques including, but not limited to, transfernin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun", and DEAE- or calcium phosphate-mediated transfection.

If the expression product is mRNA, the reagent is preferably an antisense oligo-nucleotide or a ribozyme. Polynucleotides which express antisense oligonucleotides or ribozymes can be introduced into cells by a variety of methods, as described above. Preferably, a reagent reduces expression of HM74a gene or the activity of HM74a by at least about 10, preferably about 50, more preferably about 75, 90, or 100% relative to the absence of the reagent. The effectiveness of the mechanism chosen to decrease the level of expression of HM74a gene or the activity of HM74a can be assessed using methods well known in the art, such as hybridization of nucleotide probes to HM74a-specific mRNA, quantitative RT-PCR, immunologic detection of HM74a, or measurement of HM74a activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy, including, for example, mammals such as dogs, cats, cows, horses, rabbits, monkeys, and most preferably, humans.

Nucleic acid molecules of the invention are those nucleic acid molecules which are contained in a group of nucleic acid molecules consisting of (i) nucleic acid molecules encoding a polypeptide comprising the amino acid sequence of SEQ ID NO: 2, (ii) nucleic acid molecules comprising the sequence of SEQ ID NO: 1, (iii) nucleic acid molecules having the sequence of SEQ ID NO: 1, (iv) nucleic acid molecules the complementary strand of which hybridizes under stringent conditions to a nucleic acid molecule of (i), (ii), or (iii); and (v) nucleic acid molecules the sequence of which differs from the sequence of a nucleic acid molecule of (iii) due to the degeneracy of the genetic code, wherein the polypeptide encoded by said nucleic acid molecule has HM74a activity.

Polypeptides of the invention are those polypeptides which are contained in a group of polypeptides consisting of (i) polypeptides having the sequence of SEQ ID NO: 2, (ii) polypeptides comprising the sequence of SEQ ID NO: 2, (iii) polypeptides encoded by nucleic acid molecules of the invention and (iv) polypeptides which show at least 99%, 98%, 95%, 90%, or 80% homology with a polypeptide of (i), (ii), or (iii), wherein said purified polypeptide has HM74a activity.

An object of the invention is a method of screening for therapeutic agents useful in the treatment of a disease comprised in a group of diseases consisting of disorders of the peripheral and central nervous system, cardiovascular diseases, hematological diseases, cancer, inflammation, urological diseases, respiratory diseases and gastro-enterological diseases in a mammal comprising the steps of (i) contacting a test compound with a HM74a polypeptide, (ii) detect binding of said test compound to said HM74a polypeptide. E.g., compounds that bind to the HM74a polypeptide are identified potential therapeutic agents for such a disease.

Another object of the invention is a method of screening for therapeutic agents useful in the treatment of a disease comprised in a group of diseases consisting of disorders of the peripheral and central nervous system, cardiovascular diseases, hematological diseases, cancer, inflammation, urological diseases, respiratory diseases and gastroenterological diseases in a mammal comprising the steps of (i) determining the activity of a HM74a polypeptide at a certain concentration of a test compound or in the absence of said test compound, (ii) determining the activity of said polypeptide at a different concentration of said test compound. E.g., compounds that lead to a difference in the activity of the HM74a polypeptide in (i) and (ii) are identified potential therapeutic agents for such a disease.

Another object of the invention is a method of screening for therapeutic agents useful in the treatment of a disease comprised in a group of diseases consisting of disorders of the peripheral and central nervous system, cardiovascular diseases, hematological diseases, cancer, inflammation, urological diseases, respiratory diseases and gastro-enterological diseases in a mammal comprising the steps of (i) determining the activity of a HM74a polypeptide at a certain concentration of a test compound, (ii) determining the activity of a HM74a polypeptide at the presence of a compound known to be a regulator of a HM74a polypeptide. E.g., compounds that show similar effects on the activity of the HM74a polypeptide in (i) as compared to compounds used in (ii) are identified potential therapeutic agents for such a disease.

Other objects of the invention are methods of the above, wherein the step of contacting is in or at the surface of a cell.

Other objects of the invention are methods of the above, wherein the cell is in vitro.

Other objects of the invention are methods of the above, wherein the step of contacting is in a cell-free system.

Other objects of the invention are methods of the above, wherein the polypeptide is coupled to a detectable label.

Other objects of the invention are methods of the above, wherein the compound is coupled to a detectable label.

Other objects of the invention are methods of the above, wherein the test compound displaces a ligand which is first bound to the polypeptide.

Other objects of the invention are methods of the above, wherein the polypeptide is attached to a solid support.

Other objects of the invention are methods of the above, wherein the compound is attached to a solid support.

Another object of the invention is a method of screening for therapeutic agents useful in the treatment of a disease comprised in a group of diseases consisting of disorders of the peripheral and central nervous system, cardiovascular diseases, hematological diseases, cancer, inflammation, urological diseases, respiratory diseases and gastroenterological diseases in a mammal comprising the steps of (i) contacting a test compound with a HM74a polynucleotide, (ii) detect binding of said test compound to said HM74a polynucleotide. Compounds that, e.g., bind to the HM74a polynucleotide are potential therapeutic agents for the treatment of such diseases.

Another object of the invention is the method of the above, wherein the nucleic acid molecule is RNA.

Another object of the invention is a method of the above, wherein the contacting step is in or at the surface of a cell.

Another object of the invention is a method of the above, wherein the contacting step is in a cell-free system.

Another object of the invention is a method of the above, wherein the polynucleotide is coupled to a detectable label.

Another object of the invention is a method of the above, wherein the test compound is coupled to a detectable label.

Another object of the invention is a method of diagnosing a disease comprised in a group of diseases consisting of disorders of the peripheral and central nervous system, cardiovascular diseases, hematological diseases, cancer, inflammation, urological diseases, respiratory diseases and gastro-enterological diseases in a mammal comprising the steps of (i) determining the amount of a HM74a polynucleotide in a sample taken from said mammal, (ii) determining the amount of HM74a polynucleotide in healthy and/or diseased mammal. A disease is diagnosed, e.g., if there is a substantial similarity in the amount of HM74a polynucleotide in said test mammal as compared to a diseased mammal.

Another object of the invention is a pharmaceutical composition for the treatment of a disease comprised in a group of diseases consisting of disorders of the peripheral and central nervous system, cardiovascular diseases, hematological diseases, cancer, inflammation, urological diseases, respiratory diseases and gastroenterological diseases in a mammal comprising a therapeutic agent which binds to a HM74a polypeptide.

Another object of the invention is a pharmaceutical composition for the treatment of a disease comprised in a group of diseases consisting of disorders of the peripheral and central nervous system, cardiovascular diseases, hematological diseases, cancer, inflammation, urological diseases, respiratory diseases and gastroenterological diseases in a mammal comprising a therapeutic agent which regulates the activity of a HM74a polypeptide.

Another object of the invention is a pharmaceutical composition for the treatment of a disease comprised in a group of diseases consisting of disorders of the peripheral and central nervous system, cardiovascular diseases, hematological diseases, cancer, inflammation, urological diseases, respiratory diseases and gastroenterological diseases in a mammal comprising a therapeutic agent which regulates the activity of a HM74a polypeptide, wherein said therapeutic agent is (i) a small molecule, (ii) an RNA molecule, (iii) an antisense oligonucleotide, (iv) a polypeptide, (v) an antibody, or (vi) a ribozyme.

Another object of the invention is a pharmaceutical composition for the treatment of a disease comprised in a group of diseases consisting of disorders of the peripheral and central nervous system, cardiovascular diseases, hematological diseases, cancer, inflammation, urological diseases, respiratory diseases and gastroenterological diseases in a mammal comprising a HM74a polynucleotide.

Another object of the invention is a pharmaceutical composition for the treatment of a disease comprised in a group of diseases consisting of disorders of the peripheral and central nervous system, cardiovascular diseases, hematological diseases, cancer, inflammation, urological diseases, respiratory diseases and gastroenterological diseases in a mammal comprising a HM74a polypeptide.

Another object of the invention is the use of regulators of a HM74a for the preparation of a pharmaceutical composition for the treatment of a disease comprised in a group of diseases consisting of disorders of the peripheral and central nervous system, cardiovascular diseases, hematological diseases, cancer, inflammation, urological diseases, respiratory diseases and gastroenterological diseases in a mammal.

Another object of the invention is a method for the preparation of a pharmaceutical composition useful for the treatment of a disease comprised in a group of diseases consisting of disorders of the peripheral and central nervous system, cardiovascular diseases, hematological diseases, cancer, inflammation, urological diseases, respiratory diseases and gastroenterological diseases in a mammal comprising the steps of (i) identifying a regulator of HM74a, (ii) determining whether said regulator ameliorates the symptoms of a disease comprised in a group of diseases consisting of disorders of the peripheral and central nervous system, cardiovascular diseases, hematological diseases, cancer, inflammation, urological diseases, respiratory diseases and gastroenterological diseases in a mammal; and (iii) combining of said regulator with an acceptable pharmaceutical carrier.

Another object of the invention is the use of a regulator of HM74a for the regulation of HM74a activity in a mammal having a disease comprised in a group of diseases consisting of disorders of the peripheral and central nervous system, cardiovascular diseases, hematological diseases, cancer, inflammation, urological diseases, respiratory diseases and gastroenterological diseases.

The examples below are provided to illustrate the subject invention. These examples are provided by way of illustration and are not included for the purpose of limiting the invention.

EXAMPLES

Example 1

Search for Homologous Sequences in Public Sequence Data Bases

The degree of homology can readily be calculated by known methods. Preferred methods to determine homology are designed to give the largest match between the sequences tested. Methods to determine homology are codified in publicly available computer programs such as BestFit, BLASTP, BLASTN, and FASTA. The BLAST programs are publicly available from NCBI and other sources in the internet.

For HM74a the following hits to known sequences were identified by using the BLAST algorithm [Altschul S F, Madden T L, Schaffer A A, Zhang J, Zhang Z, Miller W, Lipman D J; Nucleic Acids Res 1997 Sep. 1; 25(17): 3389-402] and the following set of parameters: matrix=BLOSUM62 and low complexity filter. The following databases were searched: NCBI (non-redundant database) and DERWENT patent database (Geneseq).

The following hits were found:

>emb|AX148194.1| Sequence 35 from Patent WO0136471, Length=1092, Score=2100 bits (1092), Expect=0.0, Identities=1092/1092 (100%)

>gb|AC026333.28| *Homo sapiens* 12 BAC RP11-324E6 (Roswell Park Cancer Institute Human BAC Library) complete sequence, Length=204793, Score=2100 bits (1092), Expect=0.0, Identities=1092/1092 (100%)

>dbj|AB065876.1| *Homo sapiens* gene for seven transmembrane helix receptor, complete cds, isolate:CBRC7TM_439, Length=1492, Score=2100 bits (1092), Expect=0.0, Identities=1092/1092 (100%)

>dbj|AB083632.1| *Homo sapiens* GPCR gene for putative G-protein coupled receptor, complete CDS, clone:hG-PCR50, Length=1092, Score=2100 bits (1092), Expect=0.0, Identities=1092/1092 (100%)

>gb|BC027965.1| *Homo sapiens,* Similar to putative chemokine receptor; GTP-binding protein, clone IMAGE:5222688, mRNA, Length=2146, Score=2094 bits (1089), Expect=0.0, Identities=1091/1092 (99%)

>dbj|BD133032.1| HM74 receptor, Length=1361, Score=2088 bits (1086), Expect=0.0, Identities=1090/1092 (99%)

>emb|AX384675.1| Sequence 15 from Patent WO0213845, Length=1179, Score=2077 bits (1080), Expect=0.0, Identities=1088/1092 (99%)

>gb|BC038955.1| *Homo sapiens,* putative chemokine receptor; GTP-binding protein, clone IMAGE:5756984, mRNA, Length=2049, Score=1948 bits (1013), Expect=0.0, Identities=1061/1085 (97%)

>dbj|AB065865.1| *Homo sapiens* gene for seven transmembrane helix receptor, complete cds, isolate:CBRC7TM_428, Length=1564, Score=1948 bits (1013), Expect=0.0, Identities=1061/1085 (97%)

>emb|AX548995.1| Sequence 280 from Patent WO02061087, Length=2051, Score=1942 bits (1010), Expect=0.0, Identities=1060/1085 (97%)

>emb|AX335595.1| Sequence 6104 from Patent WO0194629, Length=2051, Score=1942 bits (1010), Expect=0.0, Identities=1060/1085 (97%)

>emb|AX394299.1| Sequence 20 from Patent WO0218938, Length=2051, Score=1942 bits (1010), Expect=0.0, Identities=1060/1085 (97%)

>emb|AX384661.1| Sequence 1 from Patent WO0213845, Length=1174, Score=1942 bits (1010), Expect=0.0, Identities=1060/1085 (97%)
>ref|NM_006018.1| *Homo sapiens* putative chemokine receptor; GTP-binding protein (HM74), mRNA, Length=2051, Score=1942 bits (1010), Expect=0.0, Identities=1060/1085 (97%)
>dbj|D10923.1| HUMHM74 Human mRNA for HM74, Length=2051, Score=1942 bits (1010), Expect=0.0, Identities=1060/1085 (97%)
>dbj|AB065665.1| *Homo sapiens* gene for seven transmembrane helix receptor, complete cds, isolate:CBRC7TM_228, Length=1192, Score=1171 bits (609), Expect=0.0, Identities=619/624 (99%)
>ref|NM_030701.1| *Mus musculus* interferon-gamma inducible gene, Puma-g (Pumag-pending), mRNA, Length=1956, Score=1012 bits (526), Expect=0.0, Identities=862/1030 (83%)

Example 2

Expression Profiling

Total cellular RNA was isolated from cells by one of two standard methods: 1) guanidine isothiocyanate/Cesium chloride density gradient centrifugation [Kellogg, (1990)]; or with the Tri-Reagent protocol according to the manufacturer's specifications (Molecular Research Center, Inc., Cincinatti, Ohio). Total RNA prepared by the Tri-reagent protocol was treated with DNAse I to remove genomic DNA contamination.

For relative quantitation of the mRNA distribution of HM74a, total RNA from each cell or tissue source was first reverse transcribed. 85 μg of total RNA was reverse transcribed using 1 μmole random hexamer primers, 0.5 mM each of dATP, dCTP, dGTP and dTTP (Qiagen, Hilden, Germany), 3000 U RnaseQut (Invitrogen, Groningen, Netherlands) in a final volume of 680 μl. The first strand synthesis buffer and Omniscript reverse transcriptase (2 u/μl) were from (Qiagen, Hilden, Germany). The reaction was incubated at 37° C. for 90 minutes and cooled on ice. The volume was adjusted to 6800 μl with water, yielding a final concentration of 12.5 ng/μl of starting RNA.

For relative quantitation of the distribution of HM74a mRNA in cells and tissues the Applied Biosystems 7900 HT Sequence Detection system or Biorad iCycler was used according to the manufacturer's specifications and protocols. PCR reactions were set up to quantitate HM74a and the housekeeping genes BPRT (hypoxanthine phosphoribosyltransferase), GAPDH (glyceraldehyde-3-phosphate dehydrogenase), β-actin, and others. Forward and reverse primers and probes for HM74a were designed using the Perkin Elmer ABI Primer Express™ software and were synthesized by TibMolBiol (Berlin, Germany). The HM74a forward primer sequence was: Primer1 (SEQ ID NO: 3). The HM74a reverse primer sequence was Primer2 (SEQ ID NO: 4). Probe1 (SEQ ID NO: 5), labelled with FAM (carboxyfluorescein succinimidyl ester) as the reporter dye and TAMRA (carboxytetramethylrhodamine) as the quencher, is used as a probe for HM74a. The following reagents were prepared in a total of 25 μl : 1× TaqMan buffer A, 5.5 mM $MgCl_2$, 200 nM of dATP, dCTP, dGTP, and dUTP, 0.025 U/μl AmpliTaq Gold™, 0.01 U/μl AmpErase and Probe1 (SEQ ID NO: 4), HM74a forward and reverse primers each at 200 nM, 200 nM HM74a FAM/TAMRA-labelled probe, and 5 μl of template cDNA. Thermal cycling parameters were 2 min at 50° C., followed by 10 min at 95° C., followed by 40 cycles of melting at 95° C. for 15 sec and annealing/extending at 60° C. for 1 min.

Calculation of Corrected CT Values

The CT (threshold cycle) value is calculated as described in the "Quantitative determination of nucleic acids" section. The CF-value (factor for threshold cycle correction) is calculated as follows:
1. PCR reactions were set up to quantitate the housekeeping genes (HKG) for each cDNA sample.
2. $CT_{HKG}$-values (threshold cycle for housekeeping gene) were calculated as described in the "Quantitative determination of nucleic acids" section.
3. $CT_{HKG}$-mean values (CT mean value of all HKG tested on one cDNAs) of all HKG for each cDNA are calculated (n=number of HKG):

$$CT_{HKG-n}\text{-mean value}=(CT_{HKG1}\text{-value}+CT_{HKG2}\text{-value}+\ldots+CT_{HKG-n}\text{-value})/n$$

4. $CT_{pannel}$ mean value (CT mean value of all HKG in all tested cDNAs)=$(CT_{HKG1}$-mean value+$CT_{HKG2}$-mean value+. . . +$CT_{HKG-y}$-mean value)/y (y=number of cDNAs)
5. $CF_{cDNA-n}$ (correction factor for cDNA n)=$CT_{pannel}$-mean value–$CT_{HKG-n}$–mean value
6. $CT_{cDNA-n}$ (CT value of the tested gene for the cDNA n)+$CF_{cDNA-n}$ (correction factor for cDNA n)=$CT_{cor-cDNA-n}$ (corrected CT value for a gene on cDNA n)

Calculation of Relative Expression

Definition: highest $CT_{cor-cDNA-n} \neq 40$ is defined as $CT_{cor-cDNA}$ [high]

Relative Expression=$2^{(CTcor-cDNA[high]-CTcor-cDNA-n)}$

Tissues

The expression of HM74a was investigated in the tissues listed in table 1.

Expression Profile

The results of the the mRNA-quantification (expression profiling) is shown in Table 1.

TABLE 1

Relative expression of HM74a in various human tissues.

| Tissue | Relative Expression |
| --- | --- |
| fetal heart | 5 |
| heart | 357 |
| pericardium | 224 |
| heart atrium (right) | 201 |
| heart atrium (left) | 484 |
| heart ventricle (left) | 56 |
| interventricular septum | 6 |
| fetal aorta | 1 |
| aorta | 73 |
| aorta sclerotic | 79 |
| artery | 164 |
| coronary artery | 9 |
| coronary artery sclerotic | 215 |
| vein | 49 |
| coronary artery smooth muscle primary cells | 95 |
| HUVEC cells | 47 |
| skin | 1305 |
| adrenal gland | 88 |
| thyroid | 44 |
| thyroid tumor | 28 |
| pancreas | 21 |
| pancreas liver cirrhosis | 18 |
| esophagus | 101 |
| esophagus tumor | 1531 |
| stomach | 119 |
| stomach tumor | 704 |

TABLE 1-continued

Relative expression of HM74a in various human tissues.

| Tissue | Relative Expression |
|---|---|
| colon | 8 |
| colon tumor | 140 |
| small intestine | 93 |
| ileum | 94 |
| ileum tumor | 64 |
| ileum chronic inflammation | 24 |
| rectum | 488 |
| salivary gland | 129 |
| fetal liver | 41 |
| liver | 242 |
| liver liver cirrhosis | 326 |
| liver tumor | 174 |
| HEP G2 cells | 89 |
| leukocytes (peripheral blood) | 217 |
| Jurkat (T-cells) | 45 |
| bone marrow | 537 |
| erythrocytes | 137 |
| lymphnode | 158 |
| thymus | 149 |
| thrombocytes | 109 |
| bone marrow stromal cells | 24 |
| bone marrow CD71+ cells | 123 |
| bone marrow CD33+ cells | 296 |
| bone marrow CD34+ cells | 296 |
| bone marrow CD15+ cells | 549 |
| cord blood CD71+ cells | 146 |
| spleen | 1278 |
| spleen liver cirrhosis | 360 |
| skeletal muscle | 53 |
| adipose | 1663 |
| fetal brain | 53 |
| brain | 27 |
| Alzheimer brain | 187 |
| cerebellum | 2 |
| cerebellum (right) | 236 |
| cerebellum (left) | 699 |
| cerebral cortex | 197 |
| Alzheimer cerebral cortex | 50 |
| frontal lobe | 101 |
| Alzheimer brain frontal lobe | 512 |
| occipital lobe | 127 |
| parietal lobe | 9 |
| temporal lobe | 19 |
| precentral gyrus | 43 |
| postcentral gyrus | 19 |
| tonsilla cerebelli | 64 |
| vermis cerebelli | 61 |
| pons | 251 |
| substantia nigra | 165 |
| cerebral meninges | 512 |
| cerebral peduncles | 33 |
| corpus callosum | 154 |
| hippocampus | 37 |
| thalamus | 16 |
| dorsal root ganglia | 407 |
| spinal cord | 113 |
| neuroblastoma SK-N-MC cells | 256 |
| neuroblastoma SH-SY5Y cells | 133 |
| neuroblastoma IMR32 cells | 873 |
| glial tumor H4 cells | 197 |
| glial tumor H4 cells + APP | 91 |
| HEK CNS | 302 |
| HEK CNS + APP | 367 |
| retina | 39 |
| fetal lung | 53 |
| fetal lung fibroblast IMR-90 cells | 12 |
| lung | 1193 |
| lung right upper lobe | 402 |
| lung right mid lobe | 232 |
| lung right lower lobe | 232 |
| lung tumor | 568 |
| lung COPD | 133 |
| trachea | 2353 |
| cervix | 2 |
| testis | 1563 |

TABLE 1-continued

Relative expression of HM74a in various human tissues.

| Tissue | Relative Expression |
|---|---|
| HeLa cells (cervix tumor) | 17 |
| placenta | 685 |
| uterus | 147 |
| uterus tumor | 164 |
| ovary | 21 |
| ovary tumor | 1121 |
| breast | 258 |
| breast tumor | 163 |
| MDA MB 231 cells (breast tumor) | 27 |
| mammary gland | 755 |
| prostate | 197 |
| prostate BPH | 20 |
| bladder | 125 |
| ureter | 719 |
| penis | 534 |
| corpus cavernosum | 171 |
| fetal kidney | 326 |
| kidney | 885 |
| kidney tumor | 596 |
| HEK 293 cells | 32 |

Example 3

Antisense Analysis

Knowledge of the correct, complete cDNA sequence coding for HM74a enables its use as a tool for antisense technology in the investigation of gene function. Oligonucleotides, cDNA or genomic fragments comprising the antisense strand of a polynucleotide coding for HM74a are used either in vitro or in vivo to inhibit translation of the mRNA. Such technology is now well known in the art, and antisense molecules can be designed at various locations along the nucleotide sequences. By treatment of cells or whole test animals with such antisense sequences, the gene of interest is effectively turned off. Frequently, the function of the gene is ascertained by observing behavior at the intracellular, cellular, tissue or organismal level (e.g., lethality, loss of differentiated function, changes in morphology, etc.).

In addition to using sequences constructed to interrupt transcription of a particular open reading frame, modifications of gene expression is obtained by designing antisense sequences to intron regions, promoter/enhancer elements, or even to transacting regulatory genes.

Example 4

Expression of HM74a

Expression of HM74a is accomplished by subcloning the cDNAs into appropriate expression vectors and transfecting the vectors into expression hosts such as, e.g., E. coli. In a particular case, the vector is engineered such that it contains a promoter for β-galactosidase, upstream of the cloning site, followed by sequence containing the amino-terminal Methionine and the subsequent seven residues of β-galactosidase. Immediately following these eight residues is an engineered bacteriophage promoter useful for artificial priming and transcription and for providing a number of unique endonuclease restriction sites for cloning.

Induction of the isolated, transfected bacterial strain with Isopropyl-β-D-thio-galactopyranoside (IPTG) using standard methods produces a fusion protein corresponding to the first seven residues of β-galactosidase, about 15 residues of "linker", and the peptide encoded within the cDNA. Since cDNA clone inserts are generated by an essentially random process, there is probability of 33% that the included cDNA will lie in the correct reading frame for proper translation. If the cDNA is not in the proper reading frame, it is obtained by deletion or insertion of the appropriate number of bases using well known methods including in vitro mutagenesis, digestion with exonuclease in or mung bean nuclease, or the inclusion of an oligonucleotide linker of appropriate length.

The HM74a cDNA is shuttled into other vectors known to be useful for expression of proteins in specific hosts. Oligonucleotide primers containing cloning sites as well as a segment of DNA (about 25 bases) sufficient to hybridize to stretches at both ends of the target cDNA is synthesized chemically by standard methods. These primers are then used to amplify the desired gene segment by PCR. The resulting gene segment is digested with appropriate restriction enzymes under standard conditions and isolated by gel electrophoresis. Alternately, similar gene segments are produced by digestion of the cDNA with appropriate restriction enzymes. Using appropriate primers, segments of coding sequence from more than one gene are ligated together and cloned in appropriate vectors. It is possible to optimize expression by construction of such chimeric sequences.

Suitable expression hosts for such chimeric molecules include, but are not limited to, mammalian cells such as Chinese Hamster Ovary (CHO) and human 293 cells., insect cells such as Sf9 cells, yeast cells such as *Saccharomyces cerevisiae* and bacterial cells such as *E. coli*. For each of these cell systems, a useful expression vector also includes an origin of replication to allow propagation in bacteria, and a selectable marker such as the β-lactamase antibiotic resistance gene to allow plasmid selection in bacteria. In addition, the vector may include a second selectable marker such as the neomycin phosphotransferase gene to allow selection in transfected eukaryotic host cells. Vectors for use in eukaryotic expression hosts require RNA processing elements such as 3' polyadenylation sequences if such are not part of the cDNA of interest.

Additionally, the vector contains promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus enhancer, are used in mammalian host cells. Once homogeneous cultures of recombinant cells are obtained through standard culture methods, large quantities of recombinantly produced HM74a are recovered from the conditioned medium and analyzed using chromatographic methods known in the art. For example, HM74a can be cloned into the expression vector pcDNA3, as exemplified herein. This product can be used to transform, for example, HEK293 or COS by methodology standard in the art. Specifically, for example, using Lipofectamine (Gibco BRL catolog no. 18324-020) mediated gene transfer.

Example 5

Isolation of Recombinant HM74a

HM74a is expressed as a chimeric protein with one or more additional polypeptide domains added to facilitate protein purification. Such purification facilitating domains include, but are not limited to, metal chelating peptides such as histidine-tryptophan modules that allow purification on immobilized metals [Appa Rao, 1997] and the domain utilized in the FLAGS extension/affinity purification system (Immunex Corp., Seattle, Wash.). The inclusion of a cleavable linker sequence such as Factor Xa or enterokinase (Invitrogen, Groningen, The Netherlands) between the purification domain and the HM74a sequence is useful to facilitate expression of HM74a.

Example 6

Testing of Chimeric GPCRs

Functional chimeric GPCRs are constructed by combining the extracellular receptive sequences of a new isoform with the transmembrane and intracellular segments of a known isoform for test purposes. This concept was demonstrated by Kobilka et al. (1988), Science 240:1310-1316) who created a series of chimeric α2-β2 adrenergic receptors (AR) by inserting progressively greater amounts of α2-AR transmembrane sequence into β2-AR. The binding activity of known agonists changed as the molecule shifted from having more α2 than β2 conformation, and intermediate constructs demonstrated mixed specificity. The specificity for binding antagonists, however, correlated with the source of the domain VII. The importance of T7G domain VII for ligand recognition was also found in chimeras utilizing two yeast α-factor receptors and is significant because the yeast receptors are classified as miscellaneous receptors. Thus, functional role of specific domains appears to be preserved throughout the GPCR family regardless of category.

In parallel fashion, internal segments or cytoplasmic domains from a particular isoform are exchanged with the analogous domains of a known GPCRs and used to identify the structural determinants responsible for coupling the receptors to trimeric G-proteins. A chimeric receptor in which domains V, VI, and the intracellular connecting loop from β2-AR were substituted into α2-AR was shown to bind ligands with α2-AR specificity, but to stimulate adenylate cyclase in the manner of β2-AR. This demonstrates that for adrenergic-type receptors, G-protein recognition is present in domains V and VI and their connecting loop. The opposite situation was predicted and observed for a chimera in which the V→VI loop from α1-AR replaced the corresponding domain on β2-AR and the resulting receptor bound ligands with β2-AR specificity and activated G-protein-mediated phosphatidylinositol turnover in the α1-AR manner. Finally, chimeras constructed from muscarinic receptors also demonstrated that V→VI loop is the major determinant for specificity of G-protein activity.

Chimeric or modified GPCRs containing substitutions in the extracellular and transmembrane regions have shown that these portions of the receptor determine ligand binding specificity. For example, two Serine residues conserved in domain V of all adrenergic and D catecholainine GPCRs are necessary for potent agonist activity. These serines are believed to form hydrogen bonds with the catechol moiety of the agonists within the GPCR binding site. Similarly, an Asp residue present in domain III of all GPCRs which bind biogenic amines is believed to form an ion pair with the ligand amine group in the GPCR binding site.

Functional, cloned GPCRs are expressed in heterologous expression systems and their biological activity assessed. One heterologous system introduces genes for a mammalian GPCR and a mammalian G-protein into yeast cells. The GPCR is shown to have appropriate ligand specificity and affinity and trigger appropriate biological activation (growth arrest and morphological changes) of the yeast cells.

An alternate procedure for testing chimeric receptors is based on the procedure utilizing the purinergic receptor ($P_2u$). Function is easily tested in cultured K562 human leukemia cells because these cells lack $P_2u$ receptors. K562 cells are transfected with expression vectors containing either normal or chimeric $P_2u$ and loaded with fura-a, fluorescent probe for $C^{++}$. Activation of properly assembled and functional $P_2u$ receptors with extracellular UTP or ATP mobilizes intracellular $Ca^{++}$ which reacts with fura-a and is measured spectrofluorometrically.

As with the GPCRs above, chimeric genes are created by combining sequences for extracellular receptive segments of any new GPCR polypeptide with the nucleotides for the transmembrane and intracellular segments of the known $P_2u$ molecule. Bathing the transfected K562 cells in microwells containing appropriate ligands triggers binding and fluorescent activity defining effectors of the GPCR molecule. Once ligand and function are established, the $P_2u$ system is useful for defining antagonists or inhibitors which block binding and prevent such fluorescent reactions.

Example 7

Production of HM74a Specific Antibodies

Two approaches are utilized to raise antibodies to HM74a, and each approach is useful for generating either polyclonal or monoclonal antibodies. In one approach, denatured protein from reverse phase HPLC separation is obtained in quantities up to 75 mg. This denatured protein is used to immunize mice or rabbits using standard protocols; about 100 µg are adequate for immunization of a mouse, while up to 1 mg might be used to immunize a rabbit. For identifying mouse hybridomas, the denatured protein is radioiodinated and used to screen potential murine B-cell hybridomas for those which produce antibody. This procedure requires only small quantities of protein, such that 20 mg is sufficient for labeling and screening of several thousand clones.

In the second approach, the amino acid sequence of an appropriate HM74a domain, as deduced from translation of the cDNA, is analyzed to determine regions of high antigenicity. Oligopeptides comprising appropriate hydrophilic regions are synthesized and used in suitable immunization protocols to raise antibodies. The optimal amino acid sequences for immunization, are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH; Sigma, St. Louis, Mo.) by reaction with M-maleimidobenzoyl-N-hydroxysuccinimide ester, MBS. If necessary, a cysteine is introduced at the N-terminus of the peptide to permit coupling to KLH.

Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labeled (radioactive or fluorescent), affinity purified, specific goat anti-rabbit IgG.

Hybridomas are prepared and screened using standard techniques. Hybridomas of interest are detected by screening with labeled HM74a to identify those fusions producing the monoclonal antibody with the desired specificity. In a typical protocol, wells of plates (FAST; Becton-Dickinson, Palo Alto, Calif.) are coated during incubation with affinity purified, specific rabbit anti-mouse (or suitable antispecies 1 g) antibodies at 10 mg/ml. The coated wells are blocked with 1% bovine serum albumin, (BSA), washed and incubated with supernatants from hybridomas. After washing the wells are incubated with labeled HM74a at 1 mg/ml. Supernatants with specific antibodies bind more labeled HM74a than is detectable in the background. Then clones producing specific antibodies are expanded and subjected to two cycles of cloning at limiting dilution. Cloned hybridomas are injected into pristane-treated mice to produce ascites, and monoclonal antibody is purified from mouse ascitic fluid by affinity chromatography on Protein A. Monoclonal antibodies with affinities of at least $10^8$ $M^{-1}$, preferably $10^9$ to $10^{10}$ $M^{-1}$ or stronger, are typically made by standard procedures.

Example 8

Diagnostic Test Using HM74a Specific Antibodies

Particular HM74a antibodies are useful for investigating signal transduction and the diagnosis of infectious or hereditary conditions which are characterized by differences in the amount or distribution of HM74a or downstream products of an active signaling cascade.

Diagnostic tests for HM74a include methods utilizing antibody and a label to detect HM74a in human body fluids, membranes, cells, tissues or extracts of such. The polypeptides and antibodies of the present invention are used with or without modification. Frequently, the polypeptides and antibodies are labeled by joining them, either covalently or non-covalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, chromogenic agents, magnetic particles and the like.

A variety of protocols for measuring soluble or membrane-bound HM74a, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on HM74a is preferred, but a competitive binding assay may be employed.

Example 9

Purification of Native HM74a Using Specific Antibodies

Native or recombinant HM74a is purified by immunoaffinity chromatography using antibodies specific for HM74a. In general, an immunoaffinity column is constructed by covalently coupling the anti-TRH antibody to an activated chromatographic resin.

Polyclonal immunoglobulins are prepared from immune sera either by precipitation with ammonium sulfate or by purification on immobilized Protein A (Pharmacia LKB Biotechnology, Piscataway N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of HM74a by preparing a fraction from cells containing HM74a in a soluble form. This preparation is derived by solubilization of whole cells or of a subcellular fraction obtained via differential centrifugation (with or without addition of detergent) or by other methods well known in the art. Alternatively, soluble HM74a containing a signal sequence is secreted in useful quantity into the medium in which the cells are grown.

A soluble HM74a-containing preparation is passed over the immunoaffinity column, and the column is washed under conditions that allow the preferential absorbance of HM74a (e.g., high ionic strength buffers in the presence of detergent). Then, the column is eluted under conditions that disrupt antibody/protein binding (e.g., a buffer of pH 2-3 or a high concentration of a chaotrope such as urea or thiocyanate ion), and HM74a is collected.

Example 10

Drug Screening

This invention is particularly useful for screening therapeutic compounds by using HM74a or binding fragments thereof in any of a variety of drug screening techniques. As HM74a is a G protein coupled receptor any of the methods commonly used in the art may potentially be used to identify HM74a ligands. For example, the activity of a G protein coupled receptor such as HM74a can be measured using any of a variety of appropriate functional assays in which activation of the receptor results in an observable change in the level of some second messenger system, such as adenylate cyclase, guanylylcyclase, calcium mobilization, or inositol phospholipid hydrolysis. Alternatively, the polypeptide or fragment employed in such a test is either free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, are used for standard binding assays.

Measured, for example, is the formation of complexes between HM74a and the agent being tested. Alternatively, one examines the diminution in complex formation between HM74a and a ligand caused by the agent being tested.

Thus, the present invention provides methods of screening for drug canditates, drugs, or any other agents which affect signal transduction. These methods, well known in the art, comprise contacting such an agent with HM74a polypeptide or a fragment thereof and assaying (i) for the presence of a complex between the agent and HM74a polypeptide or fragment, or (ii) for the presence of a complex between HM74a polypeptide or fragment and the cell. In such competitive binding assays, the HM74a polypeptide or fragment is typically labeled. After suitable incubation, free HM74a polypeptide or fragment is separated from that present in bound form, and the amount of free or uncomplexed label is a measure of the ability of the particular agent to bind to HM74a or to interfere with the HM74a-agent complex.

Another technique for drug screening provides high throughput screening for compounds having suitable binding affinity to HM74a polypeptides. Briefly stated, large numbers of different small peptide test compounds are synthesized on a solid substrate, such as plastic pins or some other surface. The peptide test compounds are reacted with HM74a polypeptide and washed. Bound HM74a polypeptide is then detected by methods well known in the art. Purified HM74a are also coated directly onto plates for use in the aforementioned drug screening techniques. In addition, non-neutralizing antibodies are used to capture the peptide and immobilize it on the solid support.

This invention also contemplates the use of competitive drug screening assays in which neutralizing antibodies capable of binding HM74a specifically compete with a test compound for binding to HM74a polypeptides or fragments thereof. In this manner, the antibodies are used to detect the presence of any peptide which shares one or more antigenic determinants with HM74a.

Example 11

Rational Drug Design

The goal of rational drug design is to produce structural analogs of biologically active polypeptides of interest or of small molecules with which they interact, agonists, antagonists, or inhibitors. Any of these examples are used to fashion drugs which are more active or stable forms of the polypeptide or which enhance or interfere with the function of a polypeptide in vivo.

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide is gained by modeling based on the structure of homologous proteins. In both cases, relevant structural information is used to design efficient inhibitors. Useful examples of rational drug design include molecules which have improved activity or stability or which act as inhibitors, agonists, or antagonists of native peptides.

It is also possible to isolate a target-specific antibody, selected by functional assay, as described above, and then to solve its crystal structure. This approach, in principle, yields a pharmacore upon which subsequent drug design is based. It is possible to bypass protein crystallography altogether by generating anti-idiotypic antibodies (anti-ids) to a functional, pharmacologically active antibody. As a mirror image of a mirror image, the binding site of the anti-ids is expected to be an analog of the original receptor. The anti-id is then used to identify and isolate peptides from banks of chemically or biologically produced peptides. The isolated peptides then act as the pharmacore.

By virtue of the present invention, sufficient amount of polypeptide are made available to perform such analytical studies as X-ray crystallography. In addition, knowledge of the HM74a amino acid sequence provided herein provides guidance to those employing computer modeling techniques in place of or in addition to x-ray crystallography.

Example 12

Identification of Other Members of the Signal Transduction Complex

The inventive purified HM74a is a research tool for identification, characterization and purification of interacting G or other signal transduction pathway proteins. Radioactive labels are incorporated into a selected HM74a domain by various methods known in the art and used in vitro to capture interacting molecules. A preferred method involves labeling the primary amino groups in HM74a with $^{125}$I Bolton-Hunter reagent. This reagent has been used to label various molecules without concomitant loss of biological activity.

Labeled HM74a is useful as a reagent for the purification of molecules with which it interacts. In one embodiment of affinity purification, membrane-bound HM74a is covalently coupled to a chromatography column. Cell-free extract derived from synovial cells or putative target cells is passed over the column, and molecules with appropriate affinity bind to HM74a. HM74a-complex is recovered from the column, and the HM74a-binding ligand disassociated and subjected to N-terminal protein sequencing. The amino acid sequence information is then used to identify the captured molecule or to design degenerate oligonucleotide probes for cloning the relevant gene from an appropriate cDNA library.

In an alternate method, antibodies are raised against HM74a, specifically monoclonal antibodies. The monoclonal antibodies are screened to identity those which inhibit the binding of labeled HM74a. These monoclonal antibodies are then used therapeutically.

Example 13

Use and Administration of Antibodies, Inhibitors, or Antagonists

Antibodies, inhibitors, or antagonists of HM74a or other treatments and compounds that are limiters of signal transduction (LSTs), provide different effects when administered therapeutically. LSTs are formulated in a nontoxic, inert, pharmaceutically acceptable aqueous carrier medium preferably at a pH of about 5 to 8, more preferably 6 to 8, although pH may vary according to the characteristics of the antibody, inhibitor, or antagonist being formulated and the condition to be treated. Characteristics of LSTs include solubility of the molecule, its half-life and antigenicity/immunogenicity. These and other characteristics aid in defining an effective carrier. Native human proteins are preferred as LSTs, but organic or synthetic molecules resulting from drug screens are equally effective in particular situations.

LSTs are delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration is determined by the attending physician and varies according to each specific situation.

Such determinations are made by considering multiple variables such as the condition to be treated, the LST to be administered, and the pharmacokinetic profile of a particular LST. Additional factors which are taken into account include severity of the disease state, patient's age, weight, gender and diet, time and frequency of LST administration, possible combination with other drugs, reaction sensitivities, and tolerance/response to therapy. Long acting LST formulations might be administered every 3 to 4 days, every week, or once every two weeks depending on half-life and clearance rate of the particular LST.

Normal dosage amounts vary from 0.1 to $10^5$ µg, up to a total dose of about 1 g, depending upon the route of administration. Guidance as to particular dosages and methods of delivery is provided in the literature; see U.S. Pat. Nos. 4,657,760; 5,206,344; or 5,225,212. Those skilled in the art employ different formulations for different LSTs. Administration to cells such as nerve cells necessitates delivery in a manner different from that to other cells such as vascular endothelial cells.

It is contemplated that abnormal signal transduction, trauma, or diseases which trigger HM74a activity are treatable with LSTs. These conditions or diseases are specifically diagnosed by the tests discussed above, and such testing should be performed in suspected cases of viral, bacterial or fungal infections, allergic responses, mechanical injury associated with trauma, hereditary diseases, lymphoma or carcinoma, or other conditions which activate the genes of lymphoid or neuronal tissues.

Example 14

Production of Non-human Transgenic Animals

Animal model systems which elucidate the physiological and behavioral roles of the HM74a are produced by creating nonhuman transgenic animals in which the activity of the HM74a is either increased or decreased, or the amino acid sequence of the expressed HM74a is altered, by a variety of techniques. Examples of these techniques include, but are not limited to: 1) Insertion of normal or mutant versions of DNA encoding a HM74a, by microinjection, electroporation, retroviral transfection or other means well known to those skilled in the art, into appropriately fertilized embryos in order to produce a transgenic animal or 2) homologous recombination of mutant or normal, human or animal versions of these genes with the native gene locus in transgenic animals to alter the regulation of expression or the structure of these HM74a sequences. The technique of homologous recombination is well known in the art. It replaces the native gene with the inserted gene and hence is useful for producing an animal that cannot express native HM74as but does express, for example, an inserted mutant HM74a, which has replaced the native HM74a in the animal's genome by recombination, resulting in underexpression of the transporter. Microinjection adds genes to the genome, but does not remove them, and the technique is useful for producing an animal which expresses its own and added HM74a, resulting in overexpression of the HM74a One means available for producing a transgenic animal, with a mouse as an example, is as follows:. Female mice are mated, and the resulting fertilized eggs are dissected out of their oviducts. The eggs are stored in an appropriate medium such as cesium-chloride M2 medium. DNA or cDNA encoding HM74a is purified from a vector by methods well known to the one skilled in the art. Inducible promoters may be fused with the coding region of the DNA to provide an experimental means to regulate expression of the transgene. Alternatively or in addition, tissue specific regulatory elements may be fused with the coding region to permit tissue-specific expression of the transgene. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse which is a mouse stimulated by the appropriate hormones in order to maintain false pregnancy, where it proceeds to the uterus, implants, and develops to term. As noted above, microinjection is not the only method for inserting DNA into the egg but is used here only for exemplary purposes.

REFERENCES

U.S. Pat. No. 4,522,811
U.S. Pat. No. 5,283,317
U.S. Pat. No. 5,565,332
WO 84/03564
WO 92/01810
WO 93/03151
WO 94/13804
WO 00/22129
WO 01/04297
WO 01/36471
WO 01/94629
WO 02/13845
WO 02/18938
WO 02/061087
Altschul S F, Madden T L, Schaffer A A, Zhang J, Zhang Z, Miller W, Lipman D J;
Nucleic Acids Res 1997 Sep. 1; 25(17): 3389-402
Appa Rao et al., 1997, Protein Expr Purif Nov, 11(2): 201-8
Barnes, 2000, Chest, 117: 10S14S
Botstein et al., 1980, Am J Hum Genet. 32: 314-31
Colbere-Garapin et al., 1981, *J. Mol. Biol.* 150, 1-14
Engelhard et al., 1994, *Proc. Nat. Acad. Sci.* 91, 3224-3227
Gergen and Weiss, 1992, Am Rev Respir Dis 146: 823-824
Gibson et al., 1996, Genome Research 6: 995-1001
Haseloff et al., 1988, *Nature* 334, 585-591
Heid et al., 1996, Genome Research 6: 986-994
Holland et al., 1991, PNAS 88: 7276-7280
Iwabuchi et al., 1993, *Oncogene* 8, 1693-1696
Jeffreys et al., 1985, Nature 316: 76-9
Johnson et al., 1989, *Endoc. Rev.* 10, 317-331
Kellogg et al., 1990, Anal. Biochem. 189: 202-208
Lam, 1997, Anticancer Drug Res. 12(3): 145-67
Lefkowitz, 1991, *Nature* 351, 353-354
Livak et al., 1995, PCR Methods and Applications 357-362
Logan, Shenk, 1984, *Proc. Natl. Acad Sci.* 81, 3655-3659
Lowy et al., 1980, *Cell* 22, 817-23
Maddox et al., 1983, *J. Exp. Med.* 158, 1211-1216
McConnell et al., 1992, *Science* 257, 1906-1912
Nicholls et al., 1993, *J. Immunol Meth.* 165, 81-91
Pfeffer K et al., Eur J Immunol 2001 Dec;31(12): 3714-25
Piatak et al., 1993, BioTecbniques 14:70-81
Piatak et al., 1993, Science 259: 1749-1754
Pike N B et al., J Biol Chem 2003 Jan. 9
Porath et al., 1992, *Prot. Exp. Purif* 3, 263-281
Roberge et al., 1995, *Science* 269, 202-204
Sjolander, Urbaniczky, 1991, *Anal. Chem.* 63, 2338-2345
Szabo et al., 1995, *Curr. Opin. Struct. Biol.* 5, 699-705
Thomas, 1980, Proc. Nat. Acad. Sci., 77: 5201-5205
Uhlmann et al., 1987, *Tetrahedron. Lett.* 215, 3539-3542
Weber et al., 1990, Genomics 7: 524-30
Wigler et al., 1977, *Cell* 11, 223-32
Wigler et al., 1980, *Proc. Natl. Acad. Sci.* 77, 3567-70

---

The invention claimed is:

1. A method of screening for therapeutic agents which may be useful in the treatment of a peripheral nervous system disease in a mammal, comprising steps of:
   i) contacting a test compound in vitro with a HM74a polypeptide comprising the amino acid sequence SEQ ID NO:2,
   ii) detecting binding of said test compound to said HM74a polypeptide;
   iii) determining an effect of a test compound that binds to said HM74a polypeptide on a symptom of a peripheral nervous system disease in an in vivo assay; and
   iv) identifying the test compound as a potential therapeutic agent useful in the treatment of a peripheral nervous system disease if the test compound affects the symptom in the in vivo assay.

2. The method of claim 1, wherein the step of contacting is in or at the surface of a cell.

3. The method of claim 1, wherein the step of contacting is in a cell-free system.

4. The method of claim 1, wherein the polypeptide is coupled to a detectable label.

5. The method of claim 1, wherein the compound is coupled to a detectable label.

6. The method of claim 1, wherein the test compound displaces a ligand which is first bound to the polypeptide.

7. The method of claim 1, wherein the polypeptide is attached to a solid support.

8. The method of claim 1, wherein the compound is attached to a solid support.

9. A method of screening for therapeutic agents which may be useful in the treatment of a hematological disease in a mammal, comprising steps of:
   i) contacting a test compound in vitro with a HM74a polypeptide comprising the amino acid sequence SEQ ID NO:2,
   ii) detecting binding of said test compound to said HM74a polypeptide;
   iii) determining an effect of a test compound that binds to said HM74a polypeptide on a symptom of a hematological disease in an in vivo assay; and
   iv) identifying the test compound as a potential therapeutic agent useful in the treatment of a hematological disease if the test compound affects the symptom in the in vivo assay.

10. The method of claim 9, wherein the step of contacting is in or at the surface of a cell.

11. The method of claim 9, wherein the step of contacting is in a cell-free system.

12. The method of claim 9, wherein the polypeptide is coupled to a detectable label.

13. The method of claim 9, wherein the compound is coupled to a detectable label.

14. The method of claim 9, wherein the test compound displaces a ligand which is first bound to the polypeptide.

15. The method of claim 9, wherein the polypeptide is attached to a solid support.

16. The method of claim 9, wherein the compound is attached to a solid support.

* * * * *